United States Patent [19]
Martuza et al.

[11] Patent Number: 5,728,379
[45] Date of Patent: Mar. 17, 1998

[54] TUMOR- OR CELL-SPECIFIC HERPES SIMPLEX VIRUS REPLICATION

[75] Inventors: Robert L. Martuza, Chevy Chase; Samuel D. Rabkin, Bethesda, both of Md.; Shin-ichi Miyatake, Ohtsu, Japan

[73] Assignee: Georgetown University, Washington, D.C.

[21] Appl. No.: 486,147

[22] Filed: Jun. 7, 1995

Related U.S. Application Data

[63] Continuation-in-part of Ser. No. 264,581, Jun. 23, 1994, Pat. No. 5,585,096.

[51] Int. Cl.[6] .......................... A01N 63/00; A61K 48/00; C12N 15/00
[52] U.S. Cl. .................. 424/93.2; 435/172.3; 435/320.1; 935/22; 935/32
[58] Field of Search .................. 514/44; 435/172.3, 435/320.1; 424/93.2; 935/23, 32

[56] References Cited

PUBLICATIONS

Mineta et al. "Treatment Of Malignant Gliomas Using Ganciclovir–Hypersensitive, Ribonucleotide Reductase–Deficient Herpes Simplex Viral Mutant[1]", *Cancer Research*, 54:3963–66, Aug. 1, 1994.
Rabkin et al. "Transcriptional Targeting Of Herpes Simplex Virus For Cell-Specific Replication", *21st Herpesvirus Workshop Program and Abstracts*, Jul. 27–Aug. 2, 1996.
Glazenburg et al. "Construction And Properties Of Pseudorabies Virus Recombinants With Altered Control Of Immediate-Early Gene Expression", *Journal of Virology*, pp. 189–197, Jan. 1995.
Glazenburg et al. "Effects Of Replacing The Promoter Of The Immediate Early Gene With The Promoter Of Drosophila Heat–Shock Gene HSP70 On The Growth And Virulence Of Pseudorabies Virus", *Veterinary Microbiology*, 33(1992), pp. 35–43.
Sy Chung et al (1994) Mol. Cell. Differentiation 2:61–81.
RR Franks et al (1988) Genes & Development 2:1–12.
Pinkert et al., Genes & Development, vol. , pp. 268–276.
Harris et al., Gene Therapy 1: 170–175 (1994).
Brady et al., Proc. Natl. Acad. Sci. USA 91: 365–369.
Garver et al., Gene Therapy 1: 46–50 (1994).
Vile et al., Gene Therapy 1: 307–316 (1994).
Bernstein et al., Mol. Biol. Med. 6: 523–530 (1989).
Gutierrez et al., The Lancet 339: 715–721 (Mar. 21, 1992).
Vile et al., Cancer Research 53: 3860–3864 (Sep. 1, 1993).
Huber et al., Proc. Natl. Acad. Sci. USA 88: 8039–8043 (Sep. 1991).
Kuriyama et al., Cell Structure And Function 16: 503–510 (1991).
Wu et al., J. Biol. Chem., vol. 264, No. 29, pp. 16985–16987 (Oct. 15, 1989).
Smith et al., Human Gene Therapy 5: 29–35 (1994).
Hatzoglou et al., J. Of Biol. Chem., vol. 266, No. 13, pp. 8416–8425 (May 5, 1991).
Herbst et al., Proc. Natl. Acad. Sci. USA 86: 1553–1557 (Mar. 1989).

*Primary Examiner*—Bruce R. Campell
*Attorney, Agent, or Firm*—Foley & Lardner

[57] ABSTRACT

A method for killing tumor cells in vivo entails providing replication competent herpes simplex virus vectors to tumor cells. A replication competent herpes simplex virus vector, with an essential herpes simplex virus gene which is driven by a tumor-specific or cell-specific promoter that specifically destroys tumor cells and is not neurovirulent. Also, a method for producing an animal model, by ablating a specific cell type in vivo, entails providing replication competent herpes simplex virus vectors to the animal. Such a vector, with an essential herpes simplex virus gene driven by a cell- or tissue-specific promoter, specifically destroys the target cell type. This method of viral-mediated gene therapy employs cell-specific viral replication, where viral replication and associated cytotoxicity are limited to a specific cell-type by the regulated expression of an essential immediate-early (IE) viral gene product.

13 Claims, 8 Drawing Sheets

Single-Step Growth Curve

Cell cultures were infected with KOS or G92A at an MOI of 1.5 and at the times post-infection indicated, virus was harvested from the wells and titred on E5 cells.

TUMOR- OR CELL-SPECIFIC HERPES SIMPLEX VIRUS REPLICATION

BACKGROUND OF THE INVENTION

This is a continuation-in-part of U.S. application Ser. No. 08/264,581, U.S. Pat. No. 5,585,096, filed Jun. 23, 1994, the entirety of which is hereby incorporated by reference.

The present invention relates to the use of altered herpes simplex viruses that are capable of killing tumor cells. More specifically, the present invention relates to replication-competent Herpes Simplex Virus-1 (HSV-1) that contain tumor- or cell-specific transcriptional regulatory sequences which are operatively linked to an essential herpes simplex virus gene. In addition, the tumor- or cell-specific HSV-1 can be rendered non-neurovirulent and unable to replicate in non-dividing cells, yet capable of killing specific tumor cells. Also, a cell- or tissue-specific HSV-1 can also be constructed to replicate and kill a specific cell type, which is referred to as cell-specific ablation, in order to produce an animal model for a specific disease. Cell-specific ablation by cell- or tissue- specific HSV-1 can also be used to treat disorders with etiologies based on hyperactive cells or ectopically expressing cells.

In the past, viruses have been tested for their ability to treat various types of tumors in animals or humans. The proposed therapeutic mechanisms of viral cancer therapy in the prior art include: (i) producing new antigens on the tumor cell surface to induce immunologic rejection, a phenomenon called "xenogenization", and (ii) direct cell killing by the virus, called oncolysis. Austin et al., *Adv. Cancer Res.* 30: 301 (1979); Kobayashi et al., *Adv. Cancer Res.* 30: 279 (1979); Moore, Progr. *Exp. Tumor Res.* 1:411 (1960); Russell, Sem. *Cancer Biol.* 5:437–443 (1994). Treatments for tumors in both animals and in humans have been based on wild-type virus, passage-attenuated virus, or infected cell preparations. Kobayashi, *Adv. Cancer Res.* 30: 279 (1979); Cassel et al., *Cancer* 52: 856 (1983); Moore, *Prog. Exp. Tumor Res.* 1: 411 (1960).

Several animal models and animal tumors have been used to study oncolysis with wild-type viruses. Moore, *Ann. Rev. Microbiol.* 8: 393 (1954); Moore, *Progr. Exp. Tumor Res.* 1:411 (1960). At least nine viruses have been shown to be capable of inducing some degree of tumor regression in a variety of tumors in mice, rats, rabbits, and guinea pigs. A major drawback seen in these early animal studies, however, was systemic infection by the virus.

To avoid systemic infection, the genetic engineering of viruses for use as antineoplastic agents has focused on generating altered viruses that are not capable of replication in non-dividing cells. Viruses capable of replication in dividing cells preferentially kill rapidly dividing tumor cells because these viruses are incapable of replicating in non-dividing or normal cells.

The use of replication-defective retroviruses for treating tumors requires producer cells and has been shown to be limited because each replication-defective retrovirus particle can enter only a single cell and cannot productively infect others thereafter. Because these replication-defective retroviruses cannot spread to other tumor cells, they would be unable to completely penetrate a deep, multilayered tumor in vivo. Markert et al., *Neurosurg.* 77: 590 (1992).

Clinical trials employing retroviral vector therapy treatment of cancer have been approved in the United States. Culver, *Clin. Chem* 40: 510 (1994). Retroviral vector-containing cells have been implanted into brain tumors growing in human patients. Oldfield et al., *Hum. Gene Ther.* 4: 39 (1993). These retroviral vectors carried the HSV-1 thymidine kinase (HSV-tk) gene into the surrounding brain tumor cells, which conferred sensitivity of the tumor cells to the antiviral drug ganciclovir. Some of the limitations of current retroviral based cancer therapy, as described by Oldfield are: (1) the low titer of virus produced, (2) virus spread is limited to the region surrounding the producer cell implant, (3) possible immune response to the producer cell line, (4) possible insertional mutagenesis and transformation of retroviral infected cells, (5) only a single treatment regimen of pro-drug, ganciclovir, is possible because the "suicide" product kills retrovirally infected cells and producer cells and (6) the bystander effect is limited to cells in direct contact with retrovirally transformed cells. Bi, W. L. et al., *Human Gene Therapy* 4:725 (1993).

One approach to selectively expressing toxin genes in cancer cells is called "molecular chemotherapy," which employs the transcriptional regulatory sequences (TRS) of a gene expressed in the tumor to direct expression of toxin encoding sequences. Garver et al. (1994) *Gene Therapy* 1:46–50; Miller & Vile, *FASEB J.* 9:190–199 (1995). Tissue-specific regulatory sequences have been used to drive expression of "suicide genes" following (a) retroviral-mediated gene transfer, (b) direct injection of DNA or (c) adenovirus-polylysine-mediated transduction. Huber, B. E. et al. (1991) *Proc. Natl. Acad. Sci. USA* 88:8039–8043; Harris, J. D. et al. (1994). *Gene Ther.* 1: 170–175; Vile, R. et al. (1994) *Gene Ther.* 1:307–316; Smith, M. J. et al. (1994) *Human Gene Ther.* 5:29–35; Kuriyama, S. et al. (1991) *Cell Struct. Funct.* 16:503–510; Vile, R. G. et al. (1993) *Cancer Res.* 53:3860–3864; Garver, R. I. J. et al. (1994) *Gene Ther.* 1:46–50.

Retroviral-mediated gene therapy is called "virus-directed enzyme/prodrug therapy" (VDEPT). Huber, B. E. et al. (1991) *Proc. Natl. Acad. Sci. USA* 88:8039–8043; Gutierrez, A. A. et al. (1992) *The Lancet* 339:715–721. VDEPT is based on a replication-defective vector that is expressed specifically in tumor cells but not in normal cells. One in vitro example of VDEPT discriminates between normal liver and hepatoma cells by differential expression of a replication-defective retroviral vector containing the promoters for either albumin or α-fetoprotein linked to an HSV-tk gene. Huber, et al., supra. In the VDEPT system, normal liver cells were able to express thymidine kinase when the HSV-tk gene was coupled to the albumin promoter but not when coupled to the α-fetoprotein promoter. Conversely, hepatoma cells were able to express thymidine kinase when the HSV-tk gene was coupled to the α-fetoprotein promoter but not under the albumin promoter. Thymidine kinase converts nucleoside analogs or prodrugs into potent cytotoxic agents in dividing cells. Thymidine kinase expression has been achieved in several different cell types, including lymphoma, hepatocellular carcinoma, glioma, fibrosarcoma, adenocarcinoma and melanoma. Huber, B. E. et al. (1991), supra; Mullen, C. A. et al. (1992), *PNAS* 89: 33–37; Culver, K. W., et al. (1992) *Science* 256: 1550–1552; Ram, Z., et al. (1993) *Cancer Res.* 53: 83–88; Moolten, F. L. et al. (1990) *J. Natl. Cancer Inst.* 82: 297–300 and Vile, R. G. and Hart, I. R. (1993) *Cancer Res.* 53: 3860–3864.

Gene therapy strategies for cancer have also employed a number of different delivery methods to transfer "suicide genes" or immune-modulatory genes to neoplastic cells. A major goal of these strategies is to target the expression of the transferred gene to the appropriate cell type so that normal cells are not adversely affected. For example, the TRS of a protein that is specific to differentiated respiratory epithelium, human surfactant protein A, has been used to target a toxin-producing gene into a non-small cell lung cancer cell line. Smith, M. J. et al. (1994) *Human Gene Therapy* 5: 29–35. Similarly, the TRS of the carcinoma-specific protein, secretory leukoprotease inhibitor (SLPI), has been used to target thymidine kinase expression from a plasmid in SLPI-expressing carcinomas. Garver, et al., supra.

In the early 1990's, the use of genetically engineered replication-competent HSV-1 viral vectors was first explored in the context of antitumor therapy. Martuza et al., *Science* 252: 854 (1991). A replication-competent virus has the advantage of being able to enter one tumor cell, make multiple copies, lyse the cell and spread to additional tumor cells. A thymidine kinase-deficient (TK$^-$) mutant, dlsptk, was able to destroy human malignant glioma cells in an animal brain tumor model. Martuza, supra (1991). Unfortunately, the dlsptk mutants were only moderately attenuated for neurovirulence and produce encephalitis at the doses required to kill the tumor cells adequately. Markert et al., *Neurosurgery* 32: 597 (1993). Residual neurovirulence, as evidenced by a 50% lethality of intracranially-administered, replication-deficient herpes simplex virus viral vectors at $10^6$ plaque forming units (pfu) limits the use of such vectors for tumor therapy. Furthermore, known TK$^-$HSV-1 mutants are insensitive to acyclovir and ganciclovir, the most commonly used and efficacious anti-herpetic agents.

Therefore, it remains of utmost importance to develop a safe and effective viral vector for killing tumor cells. Even though various attempts had been made to engineer a viral vector able to kill human tumor cells in vivo, conventional technology provided no viral vector with attenuated neurovirulence, at the dose required to kill tumor cells, that exhibited a hypersensitivity to antiviral agents and an inability to revert to wild-type virus.

The gene therapy and molecular chemotherapy methods of the prior art depend on an exogenous polynucleotide, or the protein translated from such an exogenous polynucleotide, to perform the therapy. Currently, no tissue- or tumor- specific viral. vector has been demonstrated using a replication-competent virus. Furthermore, no tissue- or tumor-specific HSV vector has been shown to depend on the viral vector itself to perform the therapeutic killing of the targeted tissue.

In two review articles, S. J. Russell discusses some of the difficulties encountered in using a replicating viral vector targetted to tumor cells. Russell, *Sem. Cancer Biol.* 5: 437–443 (1994); *Eur. J. Cancer* 30A: 1165–1171 (1994). Strategies for increasing the accuracy of replicating vectors have focused on retroviral vectors. The Russell review describes the manipulation of small genome viruses as oncolytic agents. The major drawback of such small genome viruses is their lack of safety, because they spread to normal tissues.

Furthermore, cell-specific expression of tk was not maintained, from a retroviral vector, when transgenic animals were generated. This suggests that cell-specific retroviral-mediated gene therapy may not function as such because once cells are transformed in situ the correct expression may be turned off. Richards & Huber, *Human Gene Therapy* 4: 143 (1993).

Conventional technology has disregarded HSV as a potential vector for targetted oncolysis because the large HSV genome is difficult to regulate. Furthermore, HSV genes do not seem to be regulated as a cellular gene would be. HSV-1 genes in the environment of cellular genomes fall into two categories of regulation; either they are regulated as immediate-early genes (known as α genes) or as early genes (known as β genes). HSV-1 genes in the cellular environment are not regulated as late genes (known as γ genes). Therefore, viral gene regulation in the environment of host chromosomes does not correspond to that of viral genes in the viral genome. This suggests that cellular promoters placed in the viral genome also would be regulated differently than in their endogenous cellular genome. McKnight et al., in CANCER CELLS 4; DNA TUMOR VIRUSES. Cold Spring Harbor (1986) 163–173. Additional prior art showed that exogenous promoters were regulated as viral promoters when placed in the context of the HSV genome. This suggested that HSV could not be targetted in a cell- or tissue-specific fashion. Panning, B. and Smiley, J. R. *J. Virol.* 63: 1929 (1989); Roemer, et al., *J. Virol.* 65: 6900 (1991). Further evidence of difficulties in targeting HSV in a cell-specific fashion comes work by Anderson et al. showing that the neuron-specific enolase (NSE) promoter is an inefficient promoter in HSV for delivering genes to CNS neurons. Anderson et al., *Cell. Mol. Neurobiol.* 13: 503 (1993); Anderson et al., *Human Gene Therapy* 3: 487 (1992).

Additional evidence that exogenous genes were not regulated in a cell-specific fashion in the context of HSV comes from experiments showing that HSV products can regulate cellular promoters. Smiley, et al., *Virology* 113: 345 (1981). For example, when the rabbit β-globin gene is introduced into fibroblasts as part of an infecting HSV genome, the gene is activated by HSV immediate early polypeptides. In view of limitations of the prior art, there exists a long-felt need for virus based therapies which can destroy cancer cells, but leave normal cells largely intact.

SUMMARY OF THE INVENTION

It is therefore an object of this invention to provide a replication-competent herpes simplex virus (HSV) that is capable of killing a specific target cell type or tumor cell in vivo by employing HSV that contains a tumor- or tissue- or cell-specific promoter that is operatively linked to an essential herpes simplex virus gene.

Still another object of the present invention is to provide a mutant HSV-1 vector that can selectively replicate in and kill a tumor cell of non-nervous tissue origin. Another object of the present invention is to provide a herpes simplex virus vector, wherein the genome of the viral vector contains a tumor- or tissue- or cell-specific promoter that is operatively linked to an essential herpes simplex virus gene.

An additional object of the present invention is the production of a mutant herpes simplex virus vector containing a tumor cell-specific promoter so that the vector can be targeted to specific tumor cells. In accomplishing any of the objects of the instant invention, the essential herpes simplex virus gene may a herpes simplex virus immediate-early gene. A preferred HSV immediate-early gene to be used in the vector of the invention is the essential herpes simplex virus gene is the ICP-4 gene.

In accordance with another aspect of the present invention, a method for killing tumor cells in a subject, comprising the step of administering to the subject a pharmaceutical composition that is comprised of (A) a herpes simplex virus vector that contains a tumor-specific promoter that is operatively linked to an essential herpes simplex virus gene; and (B) a pharmaceutically acceptable vehicle for the vector, such that the tumor cells are altered in situ by the vector, whereby the tumor cells are killed. Yet another aspect of the present invention is directed to a method has been provided for killing tumor cells in a subject, comprising the step of administering to the subject a pharmaceutical composition comprising (A) a herpes simplex virus vector that is altered in (i) the ICP4 gene so that ICP4 is regulated by a tumor-specific transcriptional regulatory sequence and (ii) the γ34.5 gene, and/or (iii) the ribonucleotide reductase gene; and (B) a pharmaceutically acceptable vehicle for the vector, such that the tumor cells are altered in situ by the vector and the tumor cells are killed. The tumor cells can be of a nervous-system type selected from the group consisting of astrocytoma, oligodendroglioma, meningioma, neurofibroma, glioblastoma, ependymoma, Schwannoma, neurofibrosarcoma, and medulloblastoma. Other kinds of tumor cells which can be killed, pursuant to the present invention, include those selected from the group consisting of melanoma cells, pancreatic cancer cells, prostate carcinoma cells, breast cancer cells, lung cancer cells, colon cancer cells, gastric cancer cells, fibrosarcoma, squamous cell carcinoma, neurectodermal cells, thyroid tumor cells, pituitary tumor cells, lymphoma cells, hepatoma cells and mesothelioma, and epidermoid carcinoma cells.

In accordance with still another aspect of the present invention, a method is provided for killing tumor cells in a subject, comprising the steps of administering to the subject a herpes simplex virus vector, wherein the vector comprises a tumor-specific promoter wherein the promoter controls expression of at least one viral protein necessary for viral replication and wherein the promoter is induced selectively or at a higher level in tumor cells than in normal cells. This method can entail the use of a promoter that is selectively capable of expression in nervous-system tumor cells, for example, glioblastoma cells, medulloblastoma cells, meningioma cells, neurofibrosarcoma cells, astrocytoma cells, oligodendroglioma cells, neurofibroma cells, ependymoma cells and Schwannoma cells, as well as those nervous-system types identified above.

In satisfying these and other objects, there has been provided, in accordance with one aspect of the present invention, a replication-competent herpes simplex virus that is incapable of expressing one or both of (i) a functional γ34.5 gene product and (ii) a ribonucleotide reductase. In a preferred embodiment, the vector contains alterations in both genes.

A method also is provided for preparing a replication-competent vector of a herpes simplex virus, comprising the steps of (A) isolating a viral genome of the herpes simplex virus; and (B) permanently altering the genome so that the virus (1) kills tumor cells and (2) lacks general virulence against normal tissue/cells and (3) contains a tumor-specific promoter that is operatively linked to an essential herpes simplex virus gene. Such a vector of the instant invention also can be rendered (1) sensitive to antiviral agents and (2) capable of expressing decreased generalized neurovirulence. For example, the herpes simplex virus of the vector can be HSV-1 or HSV-2.

The present invention provides a method for ablating specific normal cells in a subject, comprising the step of administering to the subject a pharmaceutical composition that is comprised of (A) a herpes simplex virus vector that contains a tissue- or tumor- or cell-specific promoter that is operatively linked to an essential herpes simplex virus gene; and (B) a pharmaceutically acceptable vehicle for the vector, such that the specific normal cells are altered in situ by the vector, whereby the cells are killed. Such a method may be directed to ablating normal pituitary cells when the cell-specific promoter used in the HSV vector is the growth hormone promoter. Additionally, the cell ablation method may be directed to killing normal adrenocortical cells when the cell-specific promoter is Pro-opiomelanocortin.

Yet another object of the instant invention is directed to a method for killing tumor cells in a subject, comprising the steps of administering to the subject a herpes simplex virus vector, in which the vector comprises a tumor cell-specific promoter and the promoter controls expression of at least one viral protein necessary for viral replication and the promoter is induced selectively or at a higher level in tumor cells than in normal cells.

The present invention further provides for a method of protecting a subject against herpes simplex virus infection, comprising the step of administering to the subject a pharmaceutical composition that is comprised of (A) a herpes simplex virus vector wherein the genome of the virus is altered in (i) the γ34.5 gene, and (ii) the ribonucleotide reductase gene; and (B) a pharmaceutically acceptable vehicle for the vector.

In a preferred embodiment, the method further comprises the step of co-administration with neurosurgery, chemotherapy or radiotherapy.

A mutant viral vector of the present invention can be sensitive to temperatures greater than the basal temperature of the host, which provides an additional safety feature by further compromising viral replication in the presence of encephalitis and fever.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention can be understood more fully by reference to the following drawings, where.

DETAILED DESCRIPTION OF THE PREFERRED EMBODIMENTS

Figure 1:
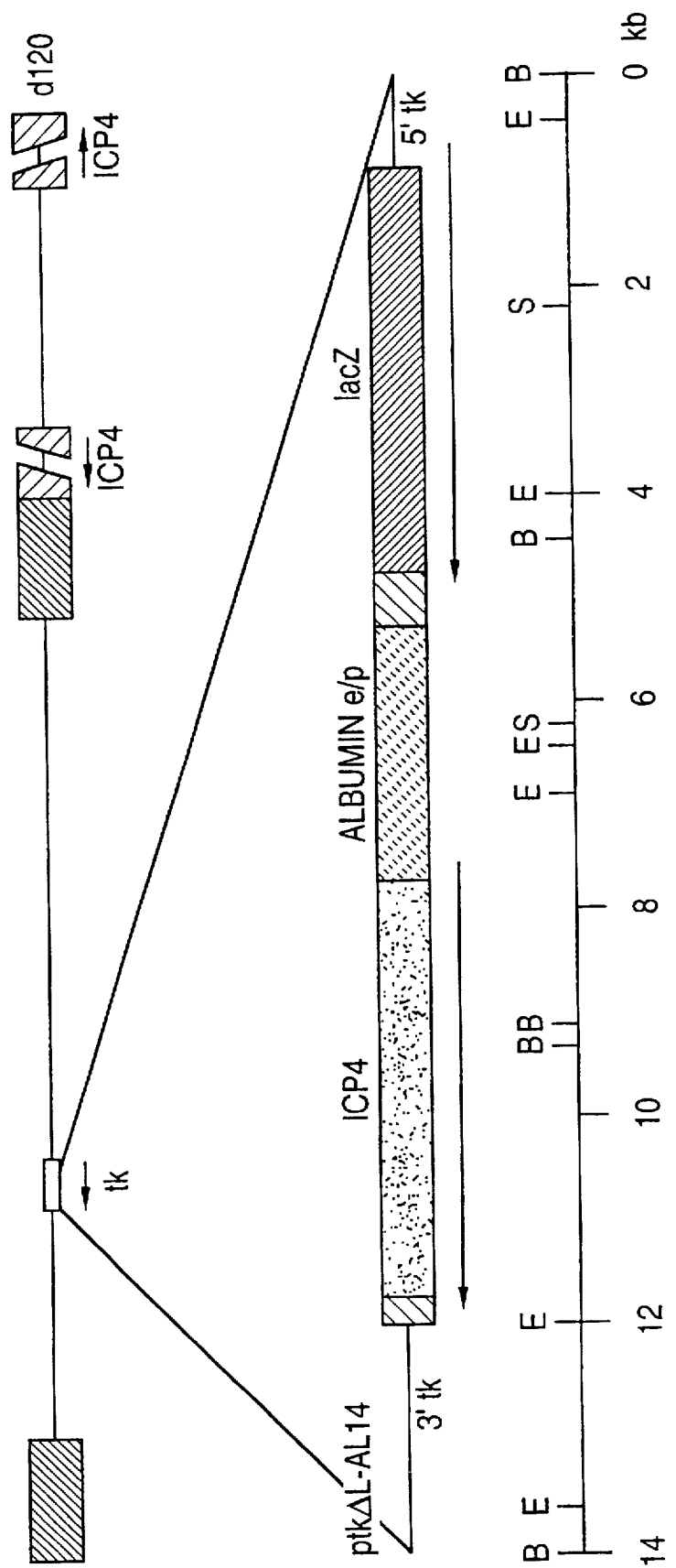
FIG. 1 is a diagram illustrating the schematic gene arrangement of G92A. The figure uses the following abbreviations: E=EcoRI, B=Bam HI, S=SspI, e/p=enhancer/promoter sequence.
Figure 2:
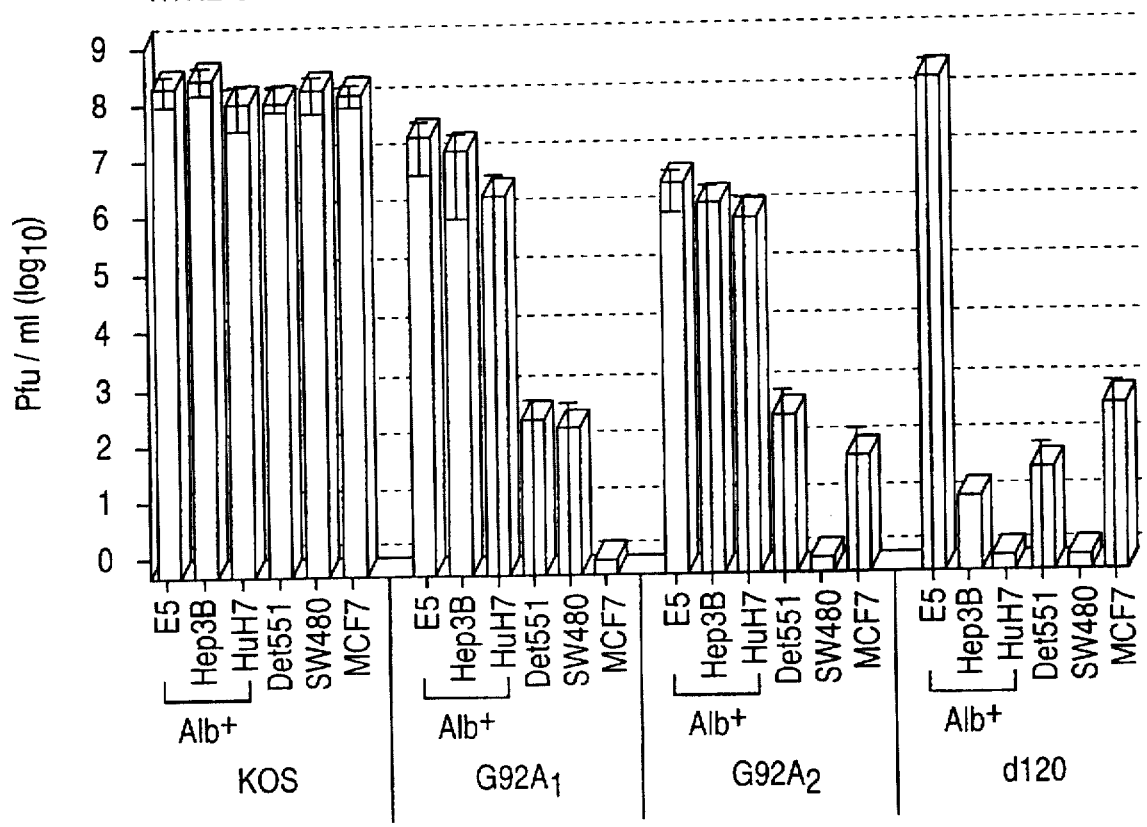
FIG. 2 is a histogram illustrating the viral infectivity of the $G92A_1$ and $G92A_2$ HSV vectors of the instant invention compared to KOS and d120 HSV vectors on different human cell types. E5 cells contain stably integrated ICP4 gene and are able to support the growth of ICP4⁻ virus. Hep3B and HuH7 are albumin expressing cells. Det551, SW480 and MCF7 are unable to express albumin. Cells were prepared in 6-well plates and the cell monolayers were infected with the indicated viruses (KOS, $G92A_1$, $G92A_2$, d120). Infected cells were incubated until plaques formed and then fixed and stained with giemsa or by X-gal histochemistry. Plaques were counted and Pfu/ml determined from the mean plaque number. The values plotted for each infected cell type are the mean of a number of different experiments, from 2 to 14.

The present invention exploits the ability of a replication-competent HSV-1 to enter a specific tumor cell or cell type in situ, make multiple copies, lyse the specific target cell and spread to additional cells of the same type with relatively minor effects on the surrounding normal cells. The herpes simplex virus of the present invention has each of the following characteristics: (1) efficacy in killing a tumor cell or normal cell type and (2) specificity for killing a specific tumor cell type or a particular normal cell type. In addition, the herpes simplex virus of the present invention may include any of the following characteristics: (a) marked attenuation of generalized neurovirulence to protect the normal brain, (b) multiple deletions so that a single mutation cannot cause reversion to the wild-type viral phenotype, and (c) hypersensitivity to ganciclovir so that undesired spread of the virus can be prevented.

The method of the prior art employ gene therapy, which is the transfer of genetic material into specific cells of a patient. Ex vivo gene therapy is gene therapy that involves the removal of the relevant target cells from the body, transduction of the cells in vitro, and subsequent reintroduction of the modified cells into the patient.

The gene therapy method of the present invention involves an in vivo method to provide a recombinant HSV to a specific target cell type or tissue. However, unlike most other methods of gene therapy that depend on an exogenous polynucleotide, or the protein translated from such an exogenous polynucleotide, to perform the therapy, the instant inventions depends on the HSV itself to perform the therapeutic killing of the targeted tissue.

The instant invention provides an alternative approach that utilizes the inherent cytotoxic capabilities of replication-competent HSV to destroy tumor cells in vivo and in the process replicate and spread throughout the tumor. Our initial studies with malignant brain tumors used mutants of HSV that were unable to replicate in non-dividing cells and/or were non-neurovirulent. Martuza, R. L. et al. (1991) *Science* 252:854–856; Mineta, T. et al. (1994) *Cancer Res.* 54:3963–3966.

Because of the inherent neuropathogenicity of HSV, non-neuropathic mutants have been isolated, which are able to grow normally in other cell types. Fawl, R. L. et al. (1994). *Sem. Virol.* 5:261–271. The differences between rapidly growing tumors and the surrounding normal brain tissue are such that virus seems to remain localized to the tumor and does not cause adverse effects on the treated animal. Martuza, R. L. et al. (1991) *Science*, supra.

Rather than target expression of a single gene product, the instant invention targets an essential viral IE gene that is required for the transcription of early and late viral genes and therefore the complete lytic growth cycle of the virus. Immediate-early genes are transcriptional/translational regulators. Examples of an essential immediate-early HSV gene include ICP4 and ICP27. (ICP27 also is known as IE63, Vmw63, IE2, UL54 and α27.) But only ICP4 is essential for turning on early viral genes. The cytotoxic potential of the vector is amplified by the synthesis of new infectious viral particles that will spread to adjacent cells throughout the tumor.

The production of cell-specific viral vectors is applicable to many systems other than tumors, such as the ablation of specific cell types in animals to produce animal models or to study the importance of a particular cell type during development by ablating particular cells at different stages in development. Thus, the method of the instant invention also is applicable to cell-specific ablation of normal cells in order to create experimental animal models for study of cell function and disease states. Cell- or tissue-specific promoters may be used in the HSV constructs of the instant invention to provide an animal model for a particular disease having an etiology based on the malfunction of such specific cells or tissues. For example, beta islet cells of the pancreas may be ablated using an HSV vector of the invention in which an essential HSV gene is regulated by the insulin promoter to produce an animal model of Insulin Dependent Diabetes Mellitus.

The disease states that have been created using knock-out transgenic mice could also be created in individual animals using the same gene used to target toxins in the knock-out transgenic mice. For example, transgenic mice have been made that contain lacZ under the control of various nervous cell specific promoters. Nirenberg, S. and Cepko, C. *J. Neurosci.* 13: 3238 (1993). In these transgenic mice, expression of lacZ could be detected with photoactivatable dye and then dye-labelled cells were photoablated.

The instant invention avoids the need for producing knock-out transgenic animals by exposing the animal to a cell-specific HSV in order to ablate specific cells in vivo. Any of the cell- or tissue-specific TRSs listed in Table 1 may be used in the claimed HSV vector. The following provide examples of cell- or tissue-specific HSV vectors: (a) the BglII$_{th}$ (−2400) to AluI$_{th}$ (+27) fragment of the rat tyrosine hydroxylase promoter (Kim, L. S., et. al. (1993). J. Biol. Chem 268: 15689–15695) can be used to produce a catecholaminergic neuron-specific HSV vector; (b) the BglI-I$_{MBP}$ (−1297) to HindIII (+60) fragment of pBP-H (Miura, M., et. al. (1989) Gene 75: 31–38) can be used to produce an oligodendrocyte-specific HSV vector; (c) BglII$_{NF-L}$ (−2003) to SmaI$_{NF-L}$ (+75) fragment of the rat light neurofilament gene (Reeben, M., et. al. (1995) J. Neurosci. Res. 40: 177–188) can be used tp produce a neuronal-specific HSV vector; (d) the SalI$_{TPH}$ (−2117) to AvaI$_{TPH}$ (+29) fragment of the human tryptophan hydroxylase gene (Boularand, S., et. al. (1995) J. Biol. Chem 270:3757–3764) can be used to produce a serotonin/pineal gland-specific HSV vector; (e) the XbaI$_{Pcp-2}$ (−3.5) to PvuI$_{Pcp2}$ (ATG) fragment of the mouse purkinje cell protein-2 (Pcp-2) gene (Vandaele, S., et. al. (1991) Genes & Dev. 5:1136–1148) can be used to produce a purkinje cell/cerebellar-specific HSV vector; (f) the SstI$_{mP1}$ (−4800) to NcoI$_{mP1}$ (+95) fragment of the mouse protamine 1 gene (Peschon, J. J., et. al. (1987) *Proc. Natl. Acad. Sci. USA* 84:5316) can be used to produce a spermatid-specific HSV vector; and (g) the pro-opiomelanocortin promoter (Tremblay et al., *Proc. Natl.*

*Acad. Sci., USA*, 85: 8890 (1988)) can be used to produce an adrenocortical cell-specific HSV. The following list provides examples of tumor-specific HSV vectors: (a) the SstI$_{EGFr}$ (−1109) to SstI$_{EGFr}$ (+1) fragment from the human epidermal growth factor receptor gene (Ishii, S. et al., PNAS 82: 4920 (1985)) can be used to produce a tumor-specific HSV vector for targeting to squamous carcinoma, glioma, or breast tumors; (b) the XmnI$_{DF3}$ (−1656) to XmnI$_{DF3}$ (+31) fragment from the human mucin-like glycoprotein gene (DF3, MUC1) (Abe, M and Kufe, D. PNAS 90:282 (1993)) can be used to produce a breast carcinoma-specific HSV vector.

In addition, the instant tumor-specific HSV vectors may be used to produce animal models for studying the physiological role of tumor-specific genes. Any of the tumor-specific TRSs or promoters listed in Table 2 may be used in the claimed HSV vector.

Yet another use for the instant cell- or tissue-specific HSV vectors is for the treatment of various disease states. Any of the cell- or tissue-specific TRSs listed in Table 1 may be used in the claimed HSV vector to ablate cells involved in a particular disease state. One potential therapeutic approach would be to ablate specific neurons involved in chronic pain. In the treatment of neuropathic pain, the HSV includes an essential HSV gene under the control of the TRS of Substance P. Such an HSV is targetted to dorsal root ganglion cells that express substance P. The HSV vector would be engineered to infect non-dividing cells and would be sensitive to an antiviral agent.

Additional therapeutic approaches include: (1) ablation of keratinocytes/epithelial cells responsible for warts; (2) ablation of cells in hyperactive organs (e.g., thyroid); (3) ablation of fat cells in obese patients (4) ablation of benign tumors (e.g., benign tumors of the thyroid, benign prostatic hypertrophy, Tuberous Sclerosis); (5) ablation of growth hormone producing adenohypophyseal cells to treat acromegaly; (6) ablation of mammotropes to stop the production of prolactin; (7) ablation of ACTH-producing cells to treat Cushing's disease; (8) ablation of epinephrine-producing chromaffin cells of the adrenal medulla to treat pheochromocytoma; and (9) ablation of insulin-producing beta islet cells to treat insulinoma.

For example, Tuberous Sclerosis is an inherited disorder (1:10,000 births) that is characterized by benign tumors (hamartomas) that invade multiple organs. Tuberous Schlerosis may be treated using an HSV vector of the invention targeted to the tumor using the αβ-crystallin transcriptional regulatory sequence. Iwaki & Tateishi, *Am. J. Pathol.* 139: 1303 (1991).

Another example utilizes the adipocyte TRS (Graves, R. A. et al., J. Cell Biochem. 49: 219 (1992).) to target the HSV vector of the invention to specifically replicate in and lyse adipocytes. For the treatment of non-cancerous cells that do not divide, the vector could not be attenuated for growth in non-dividing cells. Also, the construct should be sensitive to an antiviral agent, (e.g. tk$^+$).

Viruses of the instant invention are engineered to contain alterations in the expression of at least one essential herpes simplex virus gene. An "essential herpes simplex virus gene" is an HSV gene that encodes a protein which is essential to viral replication. See ward & Roizman, *Trends in Genetics* 10: 267 (1994). Examples of HSV genes that are essential to viral replication include the immediate-early genes ICP4 and ICP27, the genes necessary for DNA replication (VL9, VL5, VL42, DNA pol, and ICP8) and some HSV structural genes. Id. However, the HSV immediate-early genes are the preferred HSV genes to be placed under the control of the cell-, tissue- or tumor-specific promoter in the HSV of the invention. The immediate-early HSV genes ICP4 and ICP27 are preferred because they are transcriptional regulatory genes. For example, ICP4 must be turned on before the other genes essential to HSV replication. Therefore, although the HSV genes necessary for DNA replication (e.g., VL9, VL5, VL42, DNA pol and ICP8) are essential for viral replication, their placement under the control of a cell- or tissue- or tumor-specific promoter may not prove to be specific for a particular promoters or a particular cell type.

Viruses of the instant invention are engineered also to contain additional alterations in the expression of one or more specific HSV-1 genes. The specific HSV-1 genes that may be additionally altered are: (1) the γ34.5 gene and (2) the ribonucleotide reductase gene. Alterations in this regard include any that disrupt the expression of the product of both of the γ34.5 gene and the ribonucleotide reductase gene. The presence of such multiple mutations further reduces the possibility of reversion to wild-type pathogenicity.

The present invention provides methods for sequentially constructing and testing viruses for the ability to effectively kill tumor cells, including brain tumor cells, without harming surrounding normal tissue. Additionally, mutations can be inserted into these vectors to increase their sensitivity to systemically administered drugs.

Achieving Tissue- or Cell- or Tumor-Specificity

Because herpes simplex virus has a very broad host range and seems capable of infecting most cell types, herpes simplex virus mutants of the instant invention may be targeted to specific tumor types using tumor cell-specific promoters. The term "tumor cell-specific promoter" or "tumor cell-specific transcriptional regulatory sequence" or "tumor-specific promoter" or "tumor-specific transcriptional regulatory sequence" indicates a transcriptional regulatory sequence, promoter and/or enhancer that is induced selectively or at a higher level in the target tumor cell than in a normal cell. Tumor-specific promoters include promoters that are induced selectively or at a higher level in a particular cell type or a tumor cell. Tumor-cell specific TRSs that may be used in the HSV vector of the invention include those listed in Table 2. The term "tissue-specific promoter" or "cell-specific promoter" or "tissue-specific transcriptional regulatory sequence" indicates a transcriptional regulatory sequence that is induced selectively or at a higher level in the target cell or tissue type.

The vectors of the invention also can be designed to selectively replicate in and kill a tumor cell of non-nervous tissue origin. The herpes simplex virus vector of the invention is engineered to place at least one viral protein necessary for viral replication under the control of a cell-specific or tumor-specific promoter. The tumor-specific promoter is induced selectively or at higher levels in tumor cells than in normal cells.

Such tumor-specific, HSV-1 mutants utilize promoters from genes that are highly expressed in the targeted tumor, such as the epidermal growth factor receptor gene promoter (EGFr) or the basic fibroblast growth factor (bFGF) gene promoter or the NESTIN or other tumor associated promoters or enhancer elements to drive expression of an essential herpes simplex virus gene (e.g., ICP4), under circumstances in which the wild-type essential herpes simplex virus gene would not be expressed. Rendering the essential herpes simplex virus gene non-functional can be achieved by genetic inactivation or replacement of the transcriptional regulatory sequence with a tumor-specific transcriptional regulatory sequence.

The instant invention encompasses a host-range conditional herpes simplex virus mutant where an essential viral gene product is under the control of a tumor-specific promoter rather than its own viral promoter. In permissive cells, containing the proper regulatory proteins for this specific promoter, the essential viral gene product is expressed and the virus is able to replicate and spread to adjacent cells until a non-permissive cell is infected. These studies are applicable to the replication-competent herpes simplex virus of this invention. These constructs, however, are only replication-competent in the correct cell types (i.e., tumor cells or target cell type) and are replication-deficient in other cells (i.e., surrounding tissue).

Many tumor cell types express phenotypic markers which are turned off in the normal, terminally-differentiated cell. One can take advantage of this altered expression pattern to construct tumor cell-specific viruses. Examples of such differentially regulated genes in neural tumors include: (i) nestin, an intermediate filament protein normally expressed in neuroepithelial stem cells, yet not in mature CNS cells, which is ubiquitously expressed in human brain tumors, most prominently in gliomas, (ii) basic fibroblast growth factor (bFGF), a differentiation factor and mitogen for neuroectoderm, which is highly expressed in human gliomas and meningiomas but not in metastatic brain tumors or normal brain tissue and (iii) epidermal growth factor receptor (EGFr), a membrane-bound tyrosine-specific protein kinase that is stimulated by EGF, which is very often overexpressed, altered and the gene amplified in human high grade gliomas but rarely in normal brain. An example of a differentially regulated gene that is expressed in lung, breast, oropharyngeal, bladder endometrial, ovarian and colorectal carcinomas is secretory leukoprotease inhibitor (SLPI). Tables 1 and 2 provide a list of examples of tissue- and tumor-specific promoters that can be used in the vector of the instant invention.

TABLE 1

Tissue Specific Promoters

| Gene | *Species | Tissue Specificity | Ref. |
|---|---|---|---|
| alpha -Actin | Rat | mu, he | 1 |
| alpha -Actin | Rat | te, th, lu | 1 |
| Elastase - I | Rat | Pa | 2 |
| alpha -Fetoprotein | Mouse | ys, li | 3 |
| beta -Globin | Human | ery | 4 |
| beta -Globin | Rabbit | te, mu | 5 |
| beta -Globin | Rabbit | ery | 6 |
| tau -Globin | Human | ery | 7 |
| alpha -Globin | Mouse | br | 8 |
| Growth hormone | Human | pit | 9 |
| Immunoglobin- kappa | Mouse | B | 10 |
| Immunoglobin- mu | Mouse | B, T | 11 |
| Insulin | Human | beta -cells | 12 |
| Myosin Light Chain-2 | Rat | mu | 13 |
| Protamine 1 | Mouse | te | 14 |
| alpha -A-crystallin | trans | lens | 15 |
| Prolactin | * | pit | 16 |
| Pro-opiomelanocortin | * | pit | 17 |
| BTSH | * | * | 18 |
| MMTV | Mouse | breast | 19 |
| Albumin | * | li | 20 |
| Keratin | * | skin | 21 |
| Osteonectin | * | bone | 22 |
| Prostate | * | prostate | 23 |

TABLE 1-continued

Tissue Specific Promoters

| Gene | *Species | Tissue Specificity | Ref. |
|---|---|---|---|
| Olfactory Marker Protein | * | neuron | 24 |
| Neuron Specific Enolase (NSE) | * | neuron | 25 |
| L-7 | * | neuron | 26 |
| Opsin | * | retina | 27 |
| Glial Fibrillary Acidic Protein (GFAP) | human | astrocytes (CNS) | 28 |
| Tyrosine hydroxylase (TH) | rat | catecholaminergic neurons | 29 |
| | human | | 30 |
| Amyloid precursor protein (APP) | human | neurons | 31 |
| | | | 32 |
| Dopamine β-hydroxylase (DBH) | human | noradrenergic and adrenergic neurons | 33 |
| | | | 34 |
| Myelin basic protein (MBP) | mouse | oligodendrocyte | 35 |
| Light neurofilament (NF-L) | rat | neurons | 36 |
| Tryptophan hydroxylase (TPH) | human | serotonin/ pineal gland | 37 |
| | mouse | | 38 |
| Purkinje cell protein-2 (Pcp-2) | mouse | Purkinje cells/ cerebellum | 39 |
| L7 | mouse | cerebellar Purkinje retinal bipolar cells | 40 |
| Type II sodium channel | rat | neuron | 41 |
| Choline acetyltransferase (ChAT) | human | cholinergic neurons | 42 |
| | rat | | 43 |
| Neuron specific enolase (NSE) | rat | neurons | 44 |
| Aromatic L-amino acid decarboxylase (AADC) | human | catecholaminergic/ 5-HT/D-type cells | 45 |
| Protamine 1 (mP1) | mouse | spermatids | 46 |
| Proenkephalin | human | neuronal/spermatogenic epididymal cells | 47 |
| | rat | | 48 |
| reg (pancreatic stone protein) | human | colon and rectal tumors, pancreas, kidney | 49 |
| Parathyroid hormone- related peptide (PTHrP) | human | Liver and cecum tumors, neurilemoma, kidney, pancreas, adrenal | 50 |
| Stromelysin 3 | human | breast cancer | 51 |
| NSE (see nervous system) | | small-cell lung cancer, neurons | 52 |
| AADC (see nervous system) | | neurectodermal tumors | 53 |
| Albumin | | hepatoma | 54 |
| c-erbB3 | | breast cancer | |
| c-erbB4 | | breast and gastric cancer | |
| Thyroglobulin | | thyroid carcinoma | |
| α-fetoprotein | | hepatoma | 55 |
| hemoglobin | | erythrocytes | 56 |

Abbreviations: br, brain; B, lymphocytes; mu, skeletal muscle; he, cardiac muscle; te, testis; beta, beta cells; th, thymus; lu, lung; Pa, exocrine pancreas; ys, yolk sac; li, liver; ery, erythroid cells; pit, pituitary and lens, eye lens.

1. Shani, Mol. Cell. Biol., 6:2624 (1986).
2. Swift et al., Cell, 38:639 (1984).
3. Krumlauf et al., Nature, 319:224 (1985).
4. Townes et al., EMBO J., 4:1715 (1985).
5. Lacy et al., Cell, 34:343 (1983).
6. Wagner et al., Proc. Natl. Acad. Sci., U.S.A., 78:6376 (1981).
7. Brinster et al., Nature, 283:499 (1980).

8. Rusconi et al., in The Impact of Gene Transfer Techniques in Eukaryotic Cell Biology ed. J. S. Schell et al., pp. 134–152, Berlin: Springer Verlag (1984).
9. Behringer et al., Genes Dev., 2:453 (1988).
10. Storb et al., Nature, 310:238 (1984).
11. Grosschedl et al., Cell, 38:647 (1984).
12. Selden et al., Nature, 321:545 (1986).
13. Shani, Nature, 314:283 (1985).
14. Peschon et al., Ann. N. York Acad. Sci., 564:186 (1989).
15. Breitman et al., Dev., 106:457 (1989).
16. Crenshaw et al., Genes and Development, 3:959 (1989).
17. Tremblay et al., Proc. Natl. Acad. Sci., U.S.A., 85:8890 (1988).
18. Tatsumi et al., Nippon Rinsho, 47:2213 (1989).
19. Muller et al., Cell 54:105 (1988).
20. Palmiter et al., Ann. Rev. Genet., 20:465 (1986).
21. Vassar et al., Proc. Natl. Acad. Sci., U.S.A., 86:8565 (1989).
22. McVey et al., J. Biol. Chem., 263:11 (1988).
23. Allison et al., Mol. Cell. Biol., 9:2254 (1989).
24. Danciger et al., Proc. Natl. Acad. Sci., U.S.A., 86:8565 (1989).
25. Forss-Petter et al., J. Neurosci. Res., 16:141 (1986).
26. Sutcliffe, Trends in Genetics, 3:73 (1987).
27. Nathans et al., Proc. Natl. Acad. Sci., U.S.A., 81:4851 (1984).
28. Brenner, M., et al., J. Neurosci. 14:1030 (1994).
29. Kim, L. S., et al., J. Biol. Chem 268: 15689 (1993).
30. Kaneda, N., et al., Neuron 6:583 (1991).
31. Salbaum, J. M., et al., EMBO J.7:2807 (1988).
32. Wirak, D. O., et al., EMBO J. 10:289 (1990).
33. Mercer E. H., et al., Neuron 7:703 (1991).
34. Hcyle, G. W., et al., J. Neurosci. 14:2455 (1994).
35. Miura, M., et al., Gene 75: 31 (1989).
36. Reeben, M., et al., J. Neurosci. Res. 40:177 (1995).
37. Boularand, S., et al., J. Biol. Chem 270:3757 (1995).
38. Stoll, J. and Goldman, D., J. Neurosci. Res. 28:457 (1991).
39. Vandaele, S., et al., Genes & Dev. 5:1136 (1991).
40. Oberdick, J., et al., Science 248:223 (1990).
41. Maue, R. A., et al., Neuron 4:223 (1990).
42. Hersh, L. B., et al., J. Neurochem. 61:306 (1993).
43. Ibanex, C. F. and Persson, H., Eur. J. Neurosci. 3:1309 (1991).
44. Forss-Petter, S., et al., Neuron 5:187 (1990).
45. Thai, A. L. V., et al., Mol. Brain Res. 17:227 (1993).
46. Peschon, J. J., et al., Proc. Natl. Acad. Sci. U.S.A. 84:5316 (1987).
47. Borsook, D., et al., Mol. Endocrinol. 6:1502 (1992).
48. Joshi, J. and Sabol, S. L., Mol. Endocrinol. 5:1069 (1991).
49. Watanabe, T., et al., J. Biol. Chem. 265:7432 (1990).
50. Campos, R. V., et al., Mol. Rnfovtinol. 6:1642 (1992).
51. Basset, P., et al., Nature 348: 699 (1990).
52. Bombardieri, E. et al., Eur. J. Cancer 31A: 184 (1995); Koh, T. et al., Int. J. Cancer 60:843 (1995).
53. Thai, A. L. V., et al., (1993). Mol. Brain Res. 17:227.
54. Huber, B. E. PNAS 88:8099 (1991).
55. Zuibel, I. et al., J. Cell Physiol. 162:36 (1995).
56. Watanabe, T., et al., J. Biol. Chem. 265:7432 (1990).

TABLE 2

| Tumor Specific Transcriptional Regulatory Sequences | | |
|---|---|---|
| Transcriptional Regulatory Sequence/Element | target cell type(s) | Ref. |
| Secretory leukoprotease inhibitor (SLPI) | various carcinomas | Garver, R. I., Gene Therapy 1:46 (1994). |
| tyrosinase | melanoma | Vile, R. et al., Gene Therapy 1:307 (1994). Vile, R. G. WO93GB1730 Mintz, B. WO 9416557 |
| mouse serglycin | hematopoietic cell specific TR Elements | Richard L. Stevens U.S. Pat. No. 5,340,739 |
| stress inducible grp78/BiP promoter | fibrosarcoma/ tumorigenic cells | G. Gazit, et al., Cancer Res 55(8):1660 (1995). |
| ap2 adipose enhancer | adipocytes | Graves, R. A., et al., J. Cell Biochem. 49:219 (1992). |
| alpha1-antitrypsin | hepatocytes | Grayson, D. R., et al., Science 239:786 (1988). |
| transthyretin Interleukin-10 (IL-10) mRNA levels | glioblastoma multiform | Nitta, T., et al., Brain Res. 649:122 (1994). |
| c-erbB-2 | pancreatic, breast, gastric, ovarian, non-small cell lung | Harris, J. D., et al., Gene Ther. 1:170 (1994). |
| αB-crystallin/heat shock protein 27 (HSP27) | brain tumors | Aoyama, A., et al., Int. J. Cancer 55:760 (1993). |
| Basic fibroblast growth factor (bFGF) | glioma, meningioma | Shibata, F., et al., Growth Fact. 4:277 (1991). |
| Epidermal growth factor receptor (EGFr) | squamous carcinoma, glioma, breast tumor | Ishii, S., et al., Proc. Natl. Acad. Sci. USA 82:4920 (1985). |
| mucin-like glycoprotein (DF3,MUC1) | breast carcinoma | Abe, M. and Kufe, D., Proc. Natl. Acad. Sci. USA 90:282 (1993). |
| mts1 | metastatic tumors | Tulchinsky, E., et al., Proc. Natl. Acad. Sci. USA 89:9146 (1992). |
| Stromelysin 3 | breast cancer | Okada, T. et al., Proc. Natl. Sci, USA 92:2730 (1995). |
| NSE | small-cell lung cancer | Forss-Petter, S., et al., Neuron 5:187 (1990). |
| Somatostatin Receptor, NFI | small-cell lung cancer | Bombardieri, E. et al., Eur. J. Cancer 31A:184 (1995); Koh, T. et al., Int. J. Cancer 60:843 (1995). |
| Aromatic L amino acid decarboxylase (AADC) | neurecto-dermal tumors | Thai, A. L. V., et al., Mol. Brain Res. 17:227 (1993). |
| c-erbB-3, c-erbB-2 | breast cancer | Quin, C. M. et al., Histopathology 25:247 (1994); Gasparihi, P. et al., Eur. J. Cancer 30A:16 (1994). |
| c-erbB4 | breast and gastric cancer | Rajkumar, T. et al., Breast Cancer Res. Tread 29:3 (1994); Pear, C. J. et al., Year Immunol. 7:182 (1993). |
| Thyroglobulin | thyroid carcinoma | Mariotti, S. et al., J. Clin. Endocrinol. Meth. |

TABLE 2-continued

Tumor Specific Transcriptional Regulatory Sequences

| Transcriptional Regulatory Sequence/Element | target cell type(s) | Ref. |
|---|---|---|
| α-fetoprotein | hepatoma | 80:468 (1995). Zuibel, I. et al., J. Cell Physiol. 162:36 (1995). |
| Villin | gastric cancer | Osborn, M. et al., Virchows Arch. A. Pathol. Anat. Histopathol. 413:303 (1988). |
| reg (pancreatic stone protein) | colon and rectal tumors, pancreas, kidney | Watanabe, T., et al., J. Biol. Chem. 265:7432 (1990). |
| Parathyroid hormone-related peptide (PTHrP) | Liver and cecum tumors, neurilemoma, kidney, pancreas, adrenal | Campos, R. V., et al., Mol. Rnfovtinol. 6:1642 (1992). |
| Albumin | hepatoma | Huber, B. E. PNAS 88:8099 (1991). |

One specific essential HSV gene that is placed under the control of the tumor- or tissue-specific transcriptional regulatory sequence is the ICP4 gene, which is also known as the Vmw175, or IE-3, or IE175 gene or α4. ICP4 encodes a 175 kD protein that is the main trans-activator of HSV transcription and essential for lytic growth of the virus. Mutants lacking ICP4 fail to synthesize early or late viral polypeptides. Preston, C. M. (1979) J. Virol. 29:275–284. DeLuca, N. A. et al. (1985) supra.

One possible HSV backbone that is used for the recombinant vector of the instant invention is G92A, which came from d120, an HSV-1 KOS derived deletion mutant of the ICP4 gene. d120 can only grow on ICP4 complementing cell lines, such as E5. DeLuca, N. A. et al. (1985) J. Virol. 56:558–570.

To control for revertants, viral stocks are prepared on the target cell from the initial isolation of the recombinant. There would be no possibility of reversion of the ICP4 deletion, when the vector is grown on target cells. Reversions do occur, however, at low frequency in the E5 cells because E5 cells contain an integrated ICP4 gene. This strategy is used for various target cells, once it has been determined that the promoter is directing ICP4 expression in a cell-specific fashion and the recombinant has been isolated. This could be done by isolating recombinants on E5 cells first and then checking for specificity.

Not all the vectors need to be non-neurovirulent because for targeting to some tumor types, it is unlikely that the virus will get into the CNS. However, the vectors of the instant invention can also include the safety features disclosed in U.S. Pat. No. 5,585,096. The inability of the recombinant HSV to revert to wild-type is an important feature of the instant invention. Other genes may be deleted which affect the virulence of the virus or the ability to evade the host immune response. For cell-ablation, the vector is constructed so that it is able to replicate in non-dividing cells.

The effects of each construct in which a tumor- or tissue-specific transcription regulatory sequence controls an essential HSV gene is assessed in the specific mammalian target cells as well as control cells which are incapable of effecting the particular TRS.

The construction of HSV-1 vectors is described, for example, in U.S. Pat. No. 5,288,641; Roizman and Jenkins, J. Science 229: 1208 (1985); Johnson et al., J. Virol. 66: 2952 (1992); Gage et al., J. Virol. 66: 5509 (1992); Spaete and Frenkel, Cell 30; 295 (1982); Goldstein and Weller, J. Virol. 62: 196 (1988), Coen, chapter 7, Virology, Raven Press, 1990; Breakefield and DeLuca, The New Biologist, 3:203 (1991); Leib and Olivo, BioEssays 15:547 (1993); Glorioso et al., Seminars in Virology 3:265 (1992); Chou and Roizman, Proc. Natl. Acad. Sci. USA, 89:3266 (1992); Breakfield et al., Molec. Neurobiol. 1: 339 (1987); Shih et al., in: VACCINES 85, Cold Spring Harbor Press (1985) 177–180; Palella et al., Molec. Cell. Biol. 8: 457 (1988); Matz et al., J. Gen. Virol. 64: 2261 (1983); Mocarski et al., Cell 22: 243 (1980); and Coen et al., Science 234: 53 (1986).

Additional methods for the genetic manipulation of DNA sequences are known in the art. Generally, these include Ausubel et al., chapter 16 in CURRENT PROTOCOLS IN MOLECULAR BIOLOGY (John Wiley and Sons, Inc.); Paoletti et al., U.S. Pat. No. 4,603,112 (July 1986). Virological considerations also are reviewed in Coen D. M., "Molecular Genetics of Animal Viruses," in VIROLOGY 123–150 (2nd ed.) (Raven Press, 1990).

PtkΔL-ALI4, the recombinant plasmid used to generate G92A, was constructed as follows. The 0.5 kb BglII-KpnI fragment from the HSV tk coding region in pHSV106 (containing the HSV BamHI Q fragment, GIBCO/BRL Life Technologies, Gaithersburg, Md.) was replaced with a BglII-BamHI polylinker from pSL301 (Invitrogen) to generate ptkΔ. The 4.3 kb Hind III-Sal I fragment from pHCL (See Kaplitt, M. G. et al. (1991) Molecular and Cellular Neurosciences 2:320–330), containing the Escherichia coli lacZ gene and SV40 polyadenylation signal (poly A), was blunt-ended with DNA polymerase I (Klenow fragment) and subcloned into the blunt-ended g BglII site (+53 of tk) of ptkΔ to create ptkΔL. In ptkΔL lacZ expression is driven off the HSV tk promoter, an HSV early promoter. The 4.1 kb SalI-Mse I fragment of pGH108 (See Roberts, M. S. et al. (1988). J. Virol. 62:4307–4320) containing the ICP4 coding sequence, from +178 (123 bp upstream of the ATG) and polyadenylation site, was filled-in by Klenow fragment and subcloned into the blunt-ended BamHI site of p2335A-1. See, Huber, B. E. et al. (1991) supra.), 22 bases downstream of the albumin cap site (See Pinkert, C. A. et al. (1987)) to create pALI4. A 6.4 kb fragment from pALI4 (blunt-ended BstXI and EcoRV fragment), containing the albumin enhancer/promoter and ICP4 coding sequences, was subcloned into ptkΔL at the XbaI site (blunt-ended) in the polylinker just after the SV40 polyadenylation site to create ptkΔL-ALI4.

Southern Blot Hybridization Analysis of G92A DNA Structure (A) The presence of the lacZ and SV40 polyadenylation sequences were confirmed by hybridization of BamHI and SspI digested viral DNAs with labeled pHCL (containing lacZ and SV40 polyadenylation site). G92A contains the expected 3.5 and 2.2 kb fragments, not present in d120. (B) The presence of the albumin enhancer/promoter sequence was confirmed by hybridization of EcoRI digested viral DNAs with labeled p2335A-1. G92A contains the expected 2.8 and 1.8 kb fragments, not present in d120. (C) The presence of the correct ICP4 fragments was confirmed by hybridization of EcoRI digested viral DNAs with labeled pXhoI-C (containing the 9.5 kb XhoI-C fragment See O'Hare, P. et al. (1985). J. Virol. 53:751–760.), including the ICP4 gene; The native ICP4 fragments are seen with wild type HSV KOS DNA. The 4.1 kb deletion of ICP4 in d120 and G92A is contained within the 1.2 kb fragment, rather than the 5.3 kb fragment present in KOS. In addition, the 4.7 kb plasmid (ptkΔL-ALI4)-derived ICP4 fragment was seen only in G92A. (D) The lacZ, albumin enhancer/promoter and ICP4 gene insertion into the tk coding sequence was confirmed by hybridization of BamHI and SspI digested viral DNAs with labeled pHSV106 (including tk gene). The two fragments (4.5 and 2.4 kb) derived from plasmid ptkΔ-ALI4 were present in G92A, whereas the native BamHI Q fragment (3.4 kb) was present in d120.

Expression of IC4 Protein in Virus Infected Cells

E5 (ICP4-complimenting) (See DeLuca, N. A. et al. (1987) supra) HepG2, Hep3B (albumin-producing) and MCF7 (albumin non-producing) cells grown in Lab-Tek chamber slides (NUNC, Inc., Naperville, Ill.) were infected with virus, 20–100 pfu/well of G92A$_1$, G92A$_2$, d120 or hrR3 (ICP6 deletion mutant HSV). Goldstein, D. J. et al. (1988) *J. Virol.* 62:196–205. 48 hours post-infection the cells were fixed and reacted with anti-ICP4 monoclonal antibody (Advanced Biotechnologies Inc., Columbia, Md. 21046, U.S.A.) followed by ImmunoPure® Rhodamine-conjugated goat anti-mouse IgG (Pierce, Rockford, Ill. 61105). ICP4 positive cluster numbers are as following: (hrR3 infection of MCF7, E5, Hep3B and HepG2)=(6, 15, 20, 9)] and, (d120 infection of MCF7, E5, Hep3B and HepG2)=(0, 88, 0, 0), (G92A$_1$ infection of MCF5, ES, Hep3B and HepG2)=(0, 128, 28, 36) and (G92A$_2$ infection of MCF7, ES, Hep3B and HepG2)=(0, 132, 42, 70). A few individual immuno-positive cells were seen after infection of MCF7 cells with d120 and G92A. Although the lacZ gene is used as the reporter in these constructs, other reporters may be used (e.g., human placental alkaline phosphatase or other HSV gene, or neoR). β-galactosidase expression in G92A plaques.

Cells were infected with the constructs of the invention. When plaques were visible under the microscope, cells were fixed with formaldehyde/glutaraldehyde and stained with X-gal (0.5 mg/ml X-gal, 5 mM potassium ferricyanide, 5 mM potassium ferrocyanide, 2 mM MgCl$_2$ in phosphate buffered saline). β-galactosidase expressing cells appear darkly staining.

Herpes Simplex Virus Vector-Mediated Destruction of Hepatoma Cells

One example of the instant invention encompasses a hepatoma-specific herpes simplex virus mutant where an essential viral gene product is under the control of the albumin transcriptional regulatory sequence rather than its own viral promoter. More specifically, the mouse albumin enhancer/promoter sequence can be used as the cell-type specific regulatory region. Pinkert, C. A. et al. (1987) *Genes Dev.* 1:268–276; Herbst, R. S. et al. (1989) *Proc. Nat'l Acad. Sci. USA* 86:1553–1557. A region from 8.5 to 10.4 kb upstream of the albumin promoter functions as an enhancer, which in combination with the albumin promoter (300 bp), drives high-level expression in the adult liver of transgenic mice and in human hepatoma cells after infection with recombinant adenovirus or recombinant retroviruses. Herbst, R. S. et al. (1990). *Mol. Cell. Biol.* 10:3896–3905; Huber, B. E. et al. (1991) supra; Kuriyama, S. et al. (1991) supra; Pinkert, C. A. et al. (1987) supra. Albumin is expressed uniquely in the liver and it is regulated at the level of transcription initiation. Tilghman, S. M. et al. (1982). *Proc. Natl. Acad. Sci. USA* 79:5254–5257.

To construct a mutant HSV in which ICP4 is regulated by a liver-specific transcriptional regulatory sequence, a plasmid was generated, ptkΔ-ALI4, containing two chimeric genes (FIG. 1). The *E. coli* lacZ coding sequence and SV40 polyadenylation site were inserted into the HSV tk gene just downstream of the tk promoter so that β-galactosidase expression was regulated by the HSV tk promoter. The mouse albumin enhancer/promoter sequences were cloned upstream of the ICP4 coding sequence (at +178, ICP4 transcription begins at +301) and poly A addition site. Pinkert, C. A. et al. (1987) supra.

Tissue-specific promoters may be inserted into the HSV ICP4 gene at any site between the SalI site (+178) and the translation initiation site (ATG at 0). It is likely that sites upstream of +178, up to the transcription initiation site at +301 would also be functional in a cell-, tissue- or tumor-specific fashion. Using common molecular biology methods it would be possible to insert a polylinker at the SalI site in order to simplify an insertion of other promoters (by providing a range of possible restriction sites). The sequence of ICP4 with its promoter is Genbank accession number X06461, or EMBL locus id HEHSV1G3.

PtkΔ-ALI4 was linearized (at unique Sal I site in plasmid backbone) and co-transfected with d120 DNA into E5 cells (Vero cells stably transformed with the ICP4 gene (from −330 to about 400 bp downstream of 3' end of mRNA)). DeLuca, N. A. et al. (1987) *Nucleic Acids Res.* 15: 4491–4511. Recombinant viral vectors were plaque-purified three times on E5 cells. Recombinant plaques stained blue in the presence of X-gal (because of the lacZ gene) and grew in the presence of gancyclovir (1 mg/ml, because they were tk-).

Virus stocks were then prepared on HepG2 cells to minimize the possibility of contaminating the stocks with ICP4$^+$ revertants generated through recombination with the ICP4 gene present in E5 cells. Two independently isolated recombinant stocks, G92A$_1$ and G92A$_2$ were prepared. The DNA structure of these recombinants was confirmed by restriction endonuclease digestion and southern blot analysis, using probes to ICP4, lacZ, albumin enhancer/promoter and HSV tk genes. The recombinant maintains the ICP4 deletions of d120 and contains in addition the ICP4 insertion in the HSV tk gene.

In order to test the tissue specificity of the purified isolated recombinant HSVs, the viral stocks were tested for their ability to replicate in various human cell lines. Human Hep 3B (with integrated hepatitis B virus (HBV)) and HBV HepG2 and HuH7 hepatoma cells express albumin. Nakabayashi, H. et al. (1982) *Cancer Res.* 42:3858–3863; Aden, D. P. et al. (1979) *Nature* 282:615–616; Huber, B. E. et al. (1991) supra. Hepatoma cells usually have only 5–10% the level of albumin expression compared to adult hepatocytes. Clayton, D. F. et al. (1985) *Mol. Cell. Biol.* 5:2633–2641. Human MCF-7 breast adenocarcinoma cells, SW480 colon adenocarcinoma cells and Detroit 551 diploid fibroblast cells do not express detectable albumin. Huber, B. E. et al. (1991), supra.

The ability of the recombinant virus, G92A, to synthesize ICP4 protein in the various cell types was determined by immunofluorescence assay. Cells were infected with 20–100 pfu's of virus and then fixed 48 hours later. Anti-ICP4 monoclonal antibody was used to detect ICP4 expressing cells. ICP4 expression in E5 cells can only be detected after infection with HSV. Clusters of ICP4$^+$ cells are seen after infection with G92A$_1$ and G92A$_2$ only on albumin expressing cells (HepG2, Hep3B and HUH7) whereas infection with hrR3 (ICP6 deletion mutant) leads to ICP4$^+$ cell clusters in all cell types tested. Infection of non-hepatoma cells with the recombinant virus resulted in no detectable ICP4 immunoreactivity over that seen in control cells. When the plasmids were transfected into cells the number of expressing cells was similar in Vero and HepG2 cells. When plasmids containing the albumin promoter-ICP4 constructs were tested in different cell types for transient expression, no specificity was found. Immunopositivity for ICP4 identifies the gene product of the gene that is both (a) being regulated by the tumor- or tissue- or cell-specific promoter and (b) essential for replication of the virus. If the HSV construct is incapable of expressing ICP4 in the particular targetted cell type, not only would the infected cells be immunonegative for ICP4, but also there should be no plaque formation.

LacZ is used as a reporter in the instant vectors when it is regulated by an HSV early promoter (e.g. the tk promoter), which should require expression of immediate-early genes (e.g., ICP4) prior to expression. Other reporters known to those of skill in the art could be used. Examples of other potential reporters include the human placental alkaline phosphatase gene or any other HSV early or late gene for which there are specific antibodies.

The plaqueing efficiency of the recombinant virus was determined on the various cell lines. The parental wild-type strain KOS efficiently forms plaques on all the cells tested, whereas d120 only forms plaques efficiently on E5 cells (Table 5). A few plaques are formed on some of the other cell types at about $10^{-5}$ the frequency on E5 cells, probably due to revertants in the virus stock. DeLuca, N. A. et al. (1985). *J. Virol.* 56:558–570. G92A formed plaques with high efficiency on albumin-expressing hepatoma cells and with very decreased efficiency on non-expressing cells (Table 3). In addition, true plaques were not seen on the non-expressing cells but rather clusters of cells exhibiting CPE or staining with X-gal. The intensity of X-gal staining was much reduced on that seen on albumin-expressing cells. Normalizing plaqueing efficiency on the different cell types to that of wild-type KOS, a susceptibility index is obtained ranging from 0.0018 for G92A$_1$ on SW480 to 1.1 on HepG2 cells or over 600-fold difference in susceptibility.

Recombinant viral vectors, containing only the albumin enhancer/promoter ICP4 transgene, yet no lacZ reporter gene, were also isolated by growth in the presence of gancyclovir. These recombinants were also able to form plaques on hepatoma cells and expressed ICP4 protein as detected by immunofluorescence.

Figure 3:
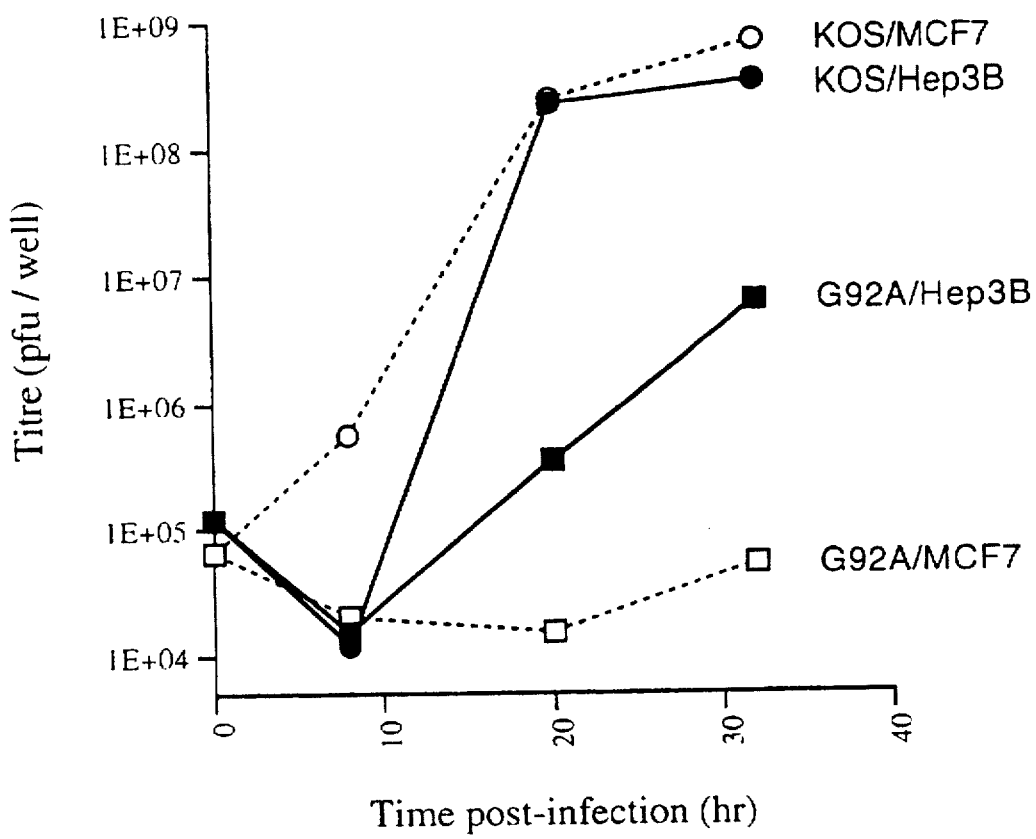
FIG. 3 is a graph illustrating a Single-Step Growth Curve in which cell cultures were infected with KOS or G92A at an MOI of 1.5 and at the times post-infection indicated, virus was harvested from the wells and titred on E5 cells.

The instant invention provides a method for constructing a virus whose lytic growth cycle is dependent upon a cell-specific regulatory element. This is demonstrated in a single step growth experiment, shown in FIG. 3, where lytic growth of G92A was seen on the albumin-expressing cells but not on control cells. G92A infection of MCF7 cells resulted in less than 1 pfu/cell, whereas when wild type KOS virus infected the same MCF7 cells, every cell produces on the order of $10^3$ pfus. When G92A infects Hep3B cells, a yield of approximately 80 pfus/cells results, indicating that lytic growth occurs in the hepatoma cell line and not in the control MCF7 cells. Wild-type virus exhibited no difference between the lytic growth in the two cell types. Thus, HSV can be constructed to be cell- or tumor-specific.

The instant invention shows that the albumin enhancer/promoter region functions in a cell-specific fashion when present within the context of the HSV genome. Some promoter elements inserted into the HSV genome are affected by the regulatory properties of the surrounding HSV sequences. Roemer, K. et al. (1991). *J. Virol.* 65:6900–6912; Panning, B. et al. (1989). *J. Virol.* 63:1929–1937. The cell-specific activity of the albumin enhancer/promoter construct within the HSV genome indicates that HSV vectors defective in replication and containing a transgene regulated by the albumin enhancer/promoter could be useful for targeted gene therapy in the liver where cell-specific gene expression without cell destruction is required.

In addition, the tumor- or tissue- specific recombinant HSV vectors of instant invention may be further include other coding sequences, such as for immune modulatory products, which can be placed under control of viral early and late promoters. The methods for producing HSV having a foreign gene product under the control of viral early and late promoter is illustrated above with lacZ. When such constructs infect the appropriate target, the foreign gene is only expressed in those cells where virus is replicating. HSV is an especially useful vector for these purposes because of its large size (with many non-essential genes) and its ability to infect most cell types. Roizman, B. et al. (1990). *Fundamental Virology*. pp. 849–896.

Plaque Forming Assay

The cells were prepared in 12-well plates and the virus stock (as indicated) was applied in a volume of 0.5 ml (except for KOS infected Hep3B, HepG2, and MCF7 which were in 6-well plates and infected with 0.7 ml). Duplicate wells were prepared for each virus dilution and two dilutions were performed for each infected cell type. Infected cells were incubated at 34.5° C. for the following times; Hep3B for 2 days, HepG2 for 6 days and HUH7, Det551, SW480, MCF7 and E5 for 3. Plaque forming units (pfu) were calculated from the mean number of plaque formed. Recombinant plaques were detected after X-gal staining. True plaques were not observed on albumin cell lines (MCF7, SW480 and Detroit 551) but rather clusters of a few cells exhibiting CPE or staining positive with X-gal. ND: not done. S.I.: susceptibility index=(ratio to E5)/(ratio to E5 for KOS).

TABLE 3

| | Titre on Different Cell Types | | | | | |
|---|---|---|---|---|---|---|
| Cells | KOS | d120 | G92A$_1$ | S.I. | G92A$_2$ | S.I. |
| E5 | 120000 50000 93000 | 240000 | 6800 | 1 | 1700 | 1 |
| HepG2 | 180000 | 0.14 | 11000 | 1.1 | 2200 | 0.9 |
| Hep3B | 97000 | 0.2 | 4200 | 0.8 | 640 | 0.5 |
| HuH7 | 25000 | 0 | 2300 | 0.7 | 610 | 0.6 |
| MCF7 | 9000 | 0 | 3.8 | 0.0008 | 2.0 | 0.002 |
| Detroit 551 | 37000 | 0.57 | 17 | 0.036 | 18 | 0.01 |
| SW480 | 8500 | ND | 10 | 0.002 | 6.8 | 0.004 |

Titre = pfu × $10^3$
S.I.: Susceptibility Index

Other Tissue-, Cell- or Tumor-Specific HSV Vectors

Another example of a recombinant HSV vector of the instant invention can be targetted to melanoma cells. The tyrosinase promoter may be cut out of the plasmid pTyr-βgall (obtained from R. Vile, St. Thomas Hospital) using EcoR1 and XhoI (EcoR1, −2540 to XhoI, −46). The tyrosinase promoter-containing fragment was then inserted upstream of ICP4 at SalI (as for G92A) by blunt ended ligation and then the tyr-ICP4 fragment inserted into the HSV tk gene (pHSV106 at the BglII/Acc651 sites) to form plasmid pT14tkΔ-1. This was then recombined into HSV d120 by homologous recombination at the tk locus and recombinant virus, rHT14 was isolated on E5 cells as GCV-resistant or by the formation of plaques on RPMI7941 cells (human malignant melanoma cells, ATCC HTB 66) or SK-MEL-3 cells (human malignant melanoma cells, ATCC HTB 69).

In vivo assessment of HSV-mediated tumor- or tissue- or cell-specific killing of target cells The effects of recombinant HSV infection on human tumors in vivo can be assessed in athymic mice to allow for growth of human tumors. The effect on animal tumors can be assessed using tumor cells from syngeneic animals. For example, human hepatoma cells can be implanted as subcutaneous xenografts in order to test the efficacy of the HSV vector G92A containing the albumin promoter/enhancer. After a period of time, approximately two to six weeks, when tumors are growing in the animals, animals are divided into two groups. One group receives intraneoplastic injection of 50 μl mock extract (Control) and a second group receives an identical injection but containing HSV vector. Tumors are measured twice weekly with Vernier calipers. Growth ratio comparisons are made to determine if the vector treated group has significantly decreased growth ratios. Animals are sacrificed for pathology when the tumor mass becomes a burden for the animal.

The presence of the HSV vector (G92A) in the tumor mass is determined using X-gal histochemistry, measuring the expression of the inserted lacZ gene, or with antibodies to viral antigens. Other organs can be examined similarly. In particular, the liver is examined to determine if the virus has spread to susceptible cell types (hepatocytes). Animals are sacrificed but not fixed so that tissues can be examined for the presence of HSV. Isolated tissue is homogenized and plated on E5 cells in order to quantitate the number of plaque forming units in the sample. Samples containing HSV will be further examined as to their growth on hepatoma cells and the presence of lacZ to indicate whether the isolated virus is the injected vector. DNA can also be isolated from such samples and the presence of vector DNA determined by PCR, using primers to the lacZ gene or the junction between HSV tk and the albumin promoter insert.

To determine the safety of the HSV vectors of the instant invention and their possible spread in vivo, animals (e.g., athymic mice, Balb/c mice and Sprague-Dawley rats) not containing tumors can be injected with the recombinant vector (G92A). Virus is administered through intravenous injection, subcutaneous injection or intraperitoneal injection. Animals are sacrificed at various times after administration of the virus (3, 7, 11, 14 day; 3, 4, and 5 weeks) and their tissues examined as discussed above.

Herpes Simplex Virus Vectors with Single Alterations in the Ribonucleotide Reductase or γ34.5 Gene Initial work on the use of attenuated herpes simplex virus vectors for use in anti-tumor therapy employed HSV-1 mutated in one gene allowing the vector to replicate in dividing cells, but not in non-dividing cells. Two such single gene-mutant herpes simplex virus vectors are (1) hrR3, deficient in ribonucleotide reductase, containing an *Escherichia coli* lacZ gene insertion in the ICP6 gene that encodes the large subunit of RR, [Mineta, T. et al., *Gene Therapy* 1: S78 (1994) and Mineta et al., *J. Neurosurg.* 80: 381 (1994)]; and (2) R3616, which contains mutations in both copies of the γ34.5 gene. Markert et al., *Neurosurgery* 32: 597 (1993).

Mutants of ribonucleotide reductase have been constructed by a number of methods. The hrR3 mutant contains an *Escherichia coli* lacZ gene insertion in the ICP6 gene, which encodes the large subunit of ribonucleotide reductase. Other ribonucleotide reductase herpes simplex virus mutants are suitable for constructing the mutant viral vector of the invention. Goldstein and Weller, supra; Goldstein and Weller, supra; Preston et al., *Virol.* 167: 458 (1988).

Ribonucleotide reductase (RR) is a key enzyme in the de novo synthesis of DNA precursors, catalyzing the reduction of ribonucleotides to deoxyribonucleotides. HSV-1 encodes its own RR (UL39 and UL40 genes), which is composed of two non- identical subunits. Duita, *J. Gen. Virol.* 64: 513 (1983). The large subunit (140 k molecular weight), designated ICP6, is tightly associated with the small subunit (38 k molecular weight). Herpes simplex virus RR is required for efficient viral growth in non-dividing cells but not in many dividing cells. Goldstein and Weller. *J. Virol.* 62:196 (1988); Goldstein and Weller, *Virol.* 166: 41 (1988); Jacobson et al., *Virol.* 173: 276 (1989). Both RR subunits are present in HSV-2. It is noted that HSV-1 ICP6 is the same as HSV-2 ICP10. Nikas et al., *Proteins* 1:376 (1986); McLaughlan and Clements *EMBO J.* 2: 1953 (1983); Swain and Halloway *J Virol.* 57: 802 (1986)] and mutations in the small subunit of RR also leads to loss of RR activity and neuropathogenicity [Cameron et al., *J. Gen. Virol.* 69: 2607 (1988)]. The presence of the lacZ gene in hrR3 allows identification of virally-infected tumor cells using β-galactosidase histochemistry.

The cytopathic effect of hrR3 (0.1 pfu/cell) on the U-87MG human glioblastoma cell line in vitro was significant; only 0.2% of U-87MG cells were alive 67 hours post-infection. For in vivo studies, ten animals harboring U-87MG tumors were randomly divided and treated intraneoplastically with either $5\times10^5$ plaque-forming units of hrR3 or with medium alone. The viral treatment group showed significant inhibition of tumor growth (p<0.01, one-sided Wilcoxon rank test).

An important difference between ribonucleotide reductase deficient (RR⁻) and other herpes simplex virus mutants is hrR3's hypersensitivity to acyclovir and ganciclovir. Because TK⁻ HSV-1 mutants known in the art are resistant to these anti-viral agents, such mutants could be difficult to eliminate in the event of systemic infection or encephalitis. Thus, in the event of viral encephalitis, hrR3 is responsive to antiviral therapy.

Also, herpes simplex virus RR– mutants are severely compromised in their ability to produce infections and synthesize viral DNA at 39.5° C. in vitro. Goldstein and Weller, *Virology* 166:41 (1988). Therefore, these mutants are attenuated for neurovirulence and less likely to propagate in the event of a fever in the infected host. Such characteristics are essential to a therapeutic vector which must be of attenuated neurovirulence and amenable to antiviral therapy in the event of viral encephalitis.

Herpes simplex virus mutants deficient in only the γ34.5 gene, such as R3616, are attenuated for neurovirulence, which reduces the possible damage to normal brain cells. Goodman et al., *J. Virol.* 63: 1153 (1989); Chou et al., *Science* 250: 1262 (1990). The decreased neurovirulence of R3616 is putatively associated with the cessation of neuronal protein synthesis, which is preempted in wild-type herpes simplex virus infection. Chou and Roizman, *Proc. Nat'l Acad. Sci. USA* 89: 3266 (1992). The γ34.5 gene product can be detected by Western blot or ELISA analysis of infected cell proteins with antibodies or lack of replication in confluent primary cells. See Bolovan et al., *J. Virol.* 68: 48 (1994). The γ34.5 gene is also present in HSV-2. McGeoch et al., *J. Gen. Virol.* 72:3057 (1991). The γ34.5 gene has been sequenced in four strains of HSV-1, namely F, 17, MGH-10 and CVG-2. Chou and Roizman, *J. Virol.* 64: 1014 (1990). The γ34.5 gene mutant HSV-1 vectors retain a wild-type level of sensitivity to acyclovir. Markert et al., supra (1993).

Mutants of γ34.5 have been constructed by various investigators using different techniques and in different strains such as mutant 1771 [McKie et al., *J. Gen. Virol.* 75: 733 (1994)] and 17termA [Bolovan et al., *J. Virol.* 68: 48 (1994)] in HSV-1 strain 17.

Construction of Herpes Simplex Virus Vectors

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state.

Replication-competent recombinant herpes simplex virus vectors of the instant invention contain alterations in expression of at least one essential herpes simplex virus gene. Viruses of the instant invention are engineered to contain additional alterations in the expression of one or more specific HSV-1 genes. The specific HSV-1 genes that may be additionally altered are: (1) the γ34.5 gene and (2) the ribonucleotide reductase gene. Alterations in the specific HSV-1 genes render the product of both genes non-functional or reduce their expression such that the mutant herpes simplex virus vector has the properties of the instant invention. Ways to achieve such alterations include (a) any method to disrupt the expression of the product of both of these genes or (b) any method to render the expressed γ34.5 gene product and ribonucleotide reductase nonfunctional.

Numerous methods known to disrupt the expression of a gene are known, including the alterations of these genes or their promoter sequences in the HSV-1 genome by insertions, deletions and/or base changes. Roizman and Jenkins, *Science* 229: 1208 (1985). The mutated herpes simplex virus vector of the instant invention is a replication competent herpes simplex virus whose genome is altered in expression of at least one essential herpes simplex virus gene. More specifically, the mutated herpes simplex virus vector of the instant invention is a replication competent herpes simplex virus whose genome is altered in expression of at least one essential herpes simplex virus gene so that the essential HSV gene is regulated by a tumor- or tissue- or cell-specific transcriptional regulatory sequence. The recombinant herpes simplex virus vector of the instant invention can be further engineered to contain additional alterations in the expression of either the γ34.5 gene or the ribonucleotide reductase gene or both of these genes.

Alterations in an essential HSV gene include modifications in the transcriptional regulatory sequences of these genes. McKnight et al. in CANCER CELLS 4; DNA TUMOR VIRUSES, Cold Spring Harbor (1986) 163–173; Post, L. E. et al., *Cell* 24: 555 (1981). Alterations in the γ34.5 gene and the ribonucleotide reductase gene include modifications in either the structural or regulatory sequences of these genes. Genetic alterations can be determined by standard methods such as Southern blot hybridization of restriction endonuclease digested viral DNA, sequencing of mutated regions of viral DNA, presence of reporter gene (for insertions), new restriction endonuclease site, enzymatic assay for ribonucleotide reductase activity [Huszar and Bacchetti, *J. Virol.* 37:580 (1981)], Western blot or ELISA analysis of infected cell proteins with antibodies to RR or γ34.5, and/or lack of replication in confluent primary cells for γ34.5. See Bolovan et al., *J. Virol.* 68: 48 (1994)] or mouse cells for RR– [Jacobson et al., *Virology* 173: 276 (1989).

The following genetic manipulations of herpes simplex virus provide examples to illustrate the production of mutant herpes simplex virus vectors. The engineering of the herpes simplex virus vectors of the instant invention well-characterized genes, the essential immediate-early (IE) ICP4, the γ34.5 and ribonucleotide reductase genes in a biologically well-characterized virus.

A herpes simplex virus vector that has been mutated in its γ34.5 and ribonucleotide reductase genes can be isolated after mutagenesis or constructed via recombination between the viral genome and genetically-engineered sequences. The high rate of recombination in herpes simplex virus and the fact that transfected viral DNA is infectious renders genetic manipulation very straightforward. These genetically-altered, replication-competent viruses can be used in the safety and efficacy assays described below.

HSV-1 contains a double-stranded, linear DNA genome, 153 kilobases in length, which has been completely sequenced by McGeoch. McGeoch et al., *J. Gen. Virol.* 69: 1531 (1988). McGeoch et al., *Nucleic Acids Res* 14: 1727 (1986); McGeoch et al., *J. Mol. Biol.* 181: 1 (1985); Perry and McGeoch, *J. Gen. Virol.* 69: 2831 (1988). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

DNA constructs employing HSV-2 based on those illustrated herein using the HSV-1 genome are encompassed by the present invention. HSV-2 contains both RR subunits; HSV-1 ICP6 is analogous to HSV-2 ICP10. Nikas et al., *Proteins* 1: 376 (1986); McLaughlan and Clements, *EMBO J.* 2: 1953 (1983); Swain and Halloway, *J. Virol.* 57: 802 (1986). γ34.5 is also present in HSV-2. McGeoch et al., *J. Gen. Virol.* 72: 3057 (1991).

Impairment of Gene Expression Via Modification of γ34.5 or Ribonucleotide Reductase Regulatory Sequences Another way to render a herpes simplex virus incapable of expressing functional γ34.5 gene product and ribonucleotide reductase is to impair their expression. The expression of these two genes can be halted by altering the regulatory sequences of the γ34.5 and ribonucleotide reductase genes.

The regulatory regions for γ34.5 and/or ribonucleotide reductase can be altered by standard techniques to disrupt the expression of the γ34.5 and ribonucleotide reductase gene. For example, their regulatory sequences could be altered within the viral genome using techniques described above for the alteration of coding sequences.

The promoter regions of γ34.5 and ribonucleotide reductase ICP6 have been mapped. The promoter for γ34.5 has been mapped to a region within the "a" sequence. The "a" sequence also contains sequences for cleavage of unit length DNA from HSV-1 concatamers, packaging of HSV-1 DNA into capsids and inversion of L and S components. Chou and Roizman, *J. Virol.* 57: 629 (1986). The promoter region of ICP6 has been mapped to the 5' upstream sequences of the ICP6 structural gene. Goldstein and Weller, *J. Virol.* 62: 196 (1988); Sze and Herman, *Virus Res.* 26: 141 (1992). The transcription start site for the small subunit of RR, namely UL40, falls within the coding region of ICP6. McLauchlan and Clements, *J. Gen. Virol.* 64: 997 (1983); McGeoch et al., *J. Gen. Virol.* 69: 1531 (1988).

The effect of these alterations on the regulatory capacity of γ34.5 and RR genes can be detected by inserting a reporter gene downstream of the promoter, such as that described for the ICP6/lacZ fusion. Goldstein and Weller, *J. Virol.* 62: 196 (1988); Sze and Herman, *Virus Res.* 26: 141 (1992). Because herpes simplex virus genes are regulated differently when present in the cellular genome, the effects of each alteration in the HSV essential gene, including ICP4, ICP27, γ34.5 or ribonucleotide reductase regulatory component would be assessed in various mammalian target cells. McKnight et al..in CANCER CELLS 4; DNA TUMOR VIRUSES, Cold Spring Harbor (1986) 163–173.

Imparting Hypersensitivity to Antiviral Agents

One safety precaution in the therapeutic use of herpes simplex virus against gliomas involves providing a means to stop any potential infection of other dividing cells. Clinical studies indicate that even wild-type HSV-1 viruses generally do not spread far from the site of initial infection or cause serious systemic disease in immunocompetent individuals. Sacks et al., *Ann. Int'l Med.* 111: 893 (1989).

It is noted that TK viruses have sometimes been associated with progressive disease in certain immunocompromised patients and that the HSV-1 mutant dlsptk is resistant to acyclovir. Erlich et al., *New Engl. J. Med.* 320: 293 (1989); Coen et al., *Proc. Nat'l Acad. Sci. USA* 86: 4736 (1989). Any mutant replication-competent viral vector that is more sensitive to the anti-viral agent than its wild-type parent is deemed hypersensitive to the anti-viral agent, potentially providing a means to abort an undesired spread of the mutant virus.

In constructing herpes simplex virus mutants for use in vivo, the mutants are tested for their sensitivity to current anti-herpetic drug therapies in order to control unforeseen virulent infections. A number of drugs currently are available to treat herpes infections in humans, the most effective being nucleoside analogs which block herpes simplex virus DNA replication. Three herpes simplex virus genes are known to be involved in sensitivity to nucleoside analogs: herpes simplex virus DNA polymerase (UL30, pol), herpes simplex virus thymidine kinase (UL23,tk), and CMV UL97 which shares homology with protein kinases and bacterial phosphotransferases. Furman et al., *J. Virol.* 32: 77 (1979); Littler et al., *Nature* 358: 160 (1992); Sullivan et al., *Nature* 358: 162 (1992).

There are a number of herpes simplex virus DNA polymerase mutants which exhibit hypersensitivity to ganciclovir, including PAA$^r$5 and AraA$^r$9. Coen et al., *J. Virol.* 53: 477 (1985). Unfortunately, intracranial injections of AraA$^r$9 led to premature death and had no effect on subcutaneous tumor growth. Markert et al., supra. Another mutant herpes simplex virus, the dlsptk virus, is no longer drug sensitive, at least to nucleoside analog drugs, and therefore potentially uncontrollable in vivo.

Attenuation for Neurovirulence

Attenuated or decreased generalized neurovirulence means that life-threatening encephalitis does not ensue after infection with the double mutant herpes simplex virus vector of the instant invention. Because herpes simplex virus-induced encephalitis in humans is very difficult to treat and can be fatal, even with adequate pharmacologic measures, decreased generalized neurovirulence is an important feature of the instant invention. The mutant virus of the present invention is capable of replicating in neoplastic cells but spares surrounding non-neoplastic tissue. Hypersensitivity to GCV need not be present with HSV constructs of the invention that are tk$^-$ because they are GCV resistant. However, one of skill in the art in view of this specification could easily place the insert, comprising the tissue- or cell- or tumor-specific promoter linked to an essential HSV gene, in another location in the HSV genome other than the tk gene. Such a vector would be GCV hypersensitive, such as G207.

For cell ablation studies, in which replication of the recombinant HSV in non-dividing cells is desired, it is likely that tk$^-$ or rr$^-$ would not work because they are attenuated for growth in non-dividing cells. For such ablation in the CNS, attenuated neurovirulence may also be a problem because the vector may not replicate in target cells.

Returning to desired attenuation of neurovirulence, the risk that a neuron-specific HSV vector for cell-specific ablation might spread to normal brain cells or other non-desired cells in the brain can be decreased by constructing HSV with a second essential gene deleted, such as a deletion in an early gene or late gene. Alternatively, the neurovirulent gene (could be deleted or placed under control of a second cell-specific promoter. For example, tk, rr or γ34.5 would be placed under control of a neuron-specific promoter (e.g. synapsin [Phiel,G. et al., *PNAS USA* 88:3431 (1991)], light neurofilament) and ICP4 would be placed under control of a second promoter specific to the subset of neurons to be targeted (e.g. tyrosine hydroxylase (TH) for catecholaminergic cell, dopamine-βhydroxylase (DBH) for noradrenergic and adrenergic neurons or Purkinje cell protein 2 (PCP-2) for Purkinje cells). Therefore, the vector of the invention would have attenuated neurovirulence when in cells other than those expressing the second cell-specific promoter.

Different herpes simplex virus strains vary in neurovirulence and more attenuated strains may be employed in the construction of the double mutant to further decrease neurovirulence. Other HSV-1 strains available from ATCC include HF (ATCCVR-260), MacIntyre (ATCCVR-539), MP (ATCCVR-735) and HSV-2 strains G (ATCC VR-734) and MS (ATCC VR-540).

Alternatively, any herpes simplex virus gene mutation leading to decreased viral replication in vivo and/or in specific cell populations may be used in the mutated herpes simplex virus vector of the invention. Other neurovirulence genes include: (i) dUTPase [Pyles et al., *J. Virol.* 66:6706, (1992)], (ii) UL53 [Moyal et al., *Virus Res.* 26:99 (1992)], (iii) α22 [Sears et al., *J. Virol.* 55: 338 (1985)] and (iv) US3 [Meignier et al., *Virology* 162:251 (1988)].

From a clinical perspective, herpes simplex virus encephalitis is the most commonly reported viral infection of the central nervous system (CNS) in the United States, with an estimated incidence of 2.3 cases per million population. Herpes simplex virus encephalitis is usually localized to the temporal lobe and the limbic system and histological examination of autopsy cases demonstrates viral antigen at these sites. A number of drugs are available to control infection, including acyclovir 9-92-hydroxyethoxy-methyl) guanine, Zovirax®, adenine arabinoside (Vidarabine®), foscarnet (phosphonoformic acid, PFA) and ganciclovir 9(1,3-dehydroxy-2-propoxy)methylguanine, DHPG, 2'NDG, Cytovene®. See Whitley et al., in Lopez et al., (eds.) IMMUNOBIOLOGY AND PROPHYLAXIS OF HUMAN HERPESVIRUS INFECTIONS, page 243 (1990, Plenum Press, New York); Whitley et al., *N. Engl. J. Med.* 297: 289 (1977); Oberg, *Pharmacol. Ther.* 19: 387 (1983); DeArmond, *Transplant. Proc.* 23: 171 (1991).

Herpes Simplex Virus Vectors Effective for Xenogenization

The mutant herpes simplex virus vector of the instant invention can be employed in a genetic therapy against specific tumors by expressing foreign genes in a tumor-specific fashion in order to target an immune response that kills the tumor cells. Tepper and Mulé, *Human Gene Therapy* 5: 153 (1994). In addition, the instant invention employs the replication competent herpes simplex virus vector having decreased neurovirulence as a tumor cell modulator or inducer of an immune response against the tumor cells. The mutant herpes simplex virus vector of the invention can be further altered to express cytokines in the tumor target cell in order to elicit an immune response against the tumor cells. For example, a mutant herpes simplex virus vector can induce viral-mediated killing of tumor cells, which then is amplified by a cytokine-enhanced immune response, a cytokine having been expressed by the vector itself. The expression of cytokines, or other gene products, from the mutant herpes simplex virus vector would occur within hours of infection so that sufficient gene products would be synthesized prior to cell killing. Cell killing may even increase the efficacy of the anti-tumor immune response. Barba et al., *Proc. Nat'l Acad. Sci. USA* 91: 4348 (1994).

Herpes Simplex Virus Vector-Mediated Destruction of Nervous Tissue Tumor Cells

Exemplary candidates for treatment according to the present invention include, but are not limited to (i) treatment of humans and other animals suffering from tumors and neoplasms, (ii) nervous system tumors and (iii) malignant brain tumor, including astrocytoma, oligodendroglioma, meningioma, neurofibroma, glioblastoma, ependymoma, Schwannoma, neurofibrosarcoma, and medulloblastoma.

Preferentially, the treatment will be initiated by direct intraneoplastic inoculation. For tumors in the brain, MRI, CT, or other imaging guided stereotactic technique will be used to direct viral inoculation or virus will be inoculated at the time of craniotomy.

The pharmaceutical compositions of the present invention would be advantageously administered in the form of injectable compositions. A typical composition for such purpose would comprise a pharmaceutically acceptable vehicle. For instance, the composition could contain human serum albumin in a phosphate buffer containing NaCl. Other pharmaceutically acceptable carriers include aqueous solutions, non-toxic excipients, including salts, preservatives, buffers and the like. See REMINGTON'S PHARMACEUTICAL SCIENCES (15th ed.) 1405–1412 & 1461–1487, Mack Publishing Co. (1975), and THE NATIONAL FORMULARY XIV (14th ed.), American Pharmaceutical Association (1975). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, THE PHARMACOLOGICAL BASIS FOR THERAPEUTICS (7th ed.).

Typically, the herpes simplex virus vector would be prepared as injectables, either as liquid solutions or suspensions; solid forms suitable for solution in, or suspension in, liquid prior to injection may also be prepared. The preparation also may be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the vector may contain minor amounts of auxiliary substances such as wetting or emulsifying agents, pH-buffering agents, adjuvants or immunopotentiators which enhance the effectiveness of the vector vaccine.

Additional formulations which are suitable for other modes of administration include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%–95% of active ingredient, preferably 25–70%.

The term "unit dose" refers to physically discrete units suitable for use in humans, each unit containing a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are on the order of one to several hundred micrograms of active ingredient per individual. Suitable regimes for initial administration and booster shots also vary but are typified by an initial administration followed in one or two week intervals by one or more subsequent injections or other administration.

Animal Studies of Transfection In Vivo

The dosages of the pharmaceutical compositions administered according to this invention can be readily determined. Generally, the preparations of this invention should be dispensed in dosage unit form comprising between $10^7$ and $10^{10}$ pfu/ml of HSV vector in a pharmaceutically acceptable carrier per unit dosage, preferably about $10^5$ to $5 \times 10^9$ pfu/ml) of the replication-competent herpes simplex virus comprising a tumor- or tissue-specific promoter that is operatively linked to an essential herpes simplex virus gene. The desired pfu are contained in a total volume of between 0.3 and 2.0 ml of phosphate buffered saline (PBS) and administered by a variety of techniques.

The HSV vector may been introduced into animals by intratumor, intravenous, intraperitoneal, intramuscular, intratracheal, intravesicle, intraintestinal, intrarectal, intraoral, intraocular or intraarterial injections. For introduction into the bladder, the vector can be instilled into the bladder by intravesicle infusion. For introduction into the rectum, the vector can be instilled using a local enema. For introduction into the lung, the vector can be introduced by instillation through a tube, infusion, inhalation into the trachea or injection into the trachea.

EXAMPLE 1

CONSTRUCTION OF HIGHLY ATTENUATED, DOUBLE HSV MUTANTS

Viruses and cell lines

HSV-1 wild-type strain (KOS or Strain F) and HSV mutants (R3616, hrR3) were kindly provided by D. M. Coen, B. Roizman, J. Chou, and S. K. Weller. HSV-1 strain F is available as ATCC VR-733; Vero cells are available as ATCC CRL 1587. R3616, which is derived from HSV-1 strain F, contains a 1-kilobase-pair deletion in both copies of the γ34.5 gene. R3616 was constructed as described in Chou et al., *Science* 250: 1262 (1990).

Stocks of viruses were generated in African green monkey kidney cell (Vero) cultures as described. Virus stocks were prepared as described by Coen et al., *J. Virol.* 53:477 (1985).

Human glioblastoma cells U-87MG, T98G, U-138MG, and A172 were obtained from American Type Culture Collection (Rockville, Md.) and cultured in Dulbecco's minimal essential medium (DMEM) supplemented with 10% inactivated fetal calf serum (IFCS) and antibiotics. Viral DNA is isolated from infected cells, which are gently lysed with NP40, treated with RNase, then SDS and Proteinase K, and finally extracted with phenol, chloroform/isoamylalcohol, and ether. The viral DNA is suitable for transfection after precipitation with ethanol and resuspension in water. For the generation of recombinant viruses, the piece of DNA to be recombined into the viral genome is excised from a plasmid. The linear DNA is co-transfected with viral DNA into cells capable of supporting propagation of the recombinant progeny virus. When extensive cytopathic effects are observed, progeny virus is harvested. Recombinant viruses are then plated on permissive cells under selectable or screenable conditions. For example, LacZ+ recombinant plaques are stained by adding X-gal and blue plaques (LacZ+) are selected. Further plaque purification (three times) is conducted before a stock is made.

Construction of herpes simplex virus incapable of expressing both γ34.5 gene product and ribonucleotide reductase Herpes simplex virus strains mutated in both the γ34.5 and ribonucleotide reductase genes are constructed using standard procedures for the generation of viral recombinants as described by Goldstein and Weller. Both of these genes are non-essential for viral growth in culture and therefore null mutants are viable in culture. Such double mutants include the insertion of the *E. coli* Lac Z gene in either gene, so that replication in site can readily be detected.

Figure 4:
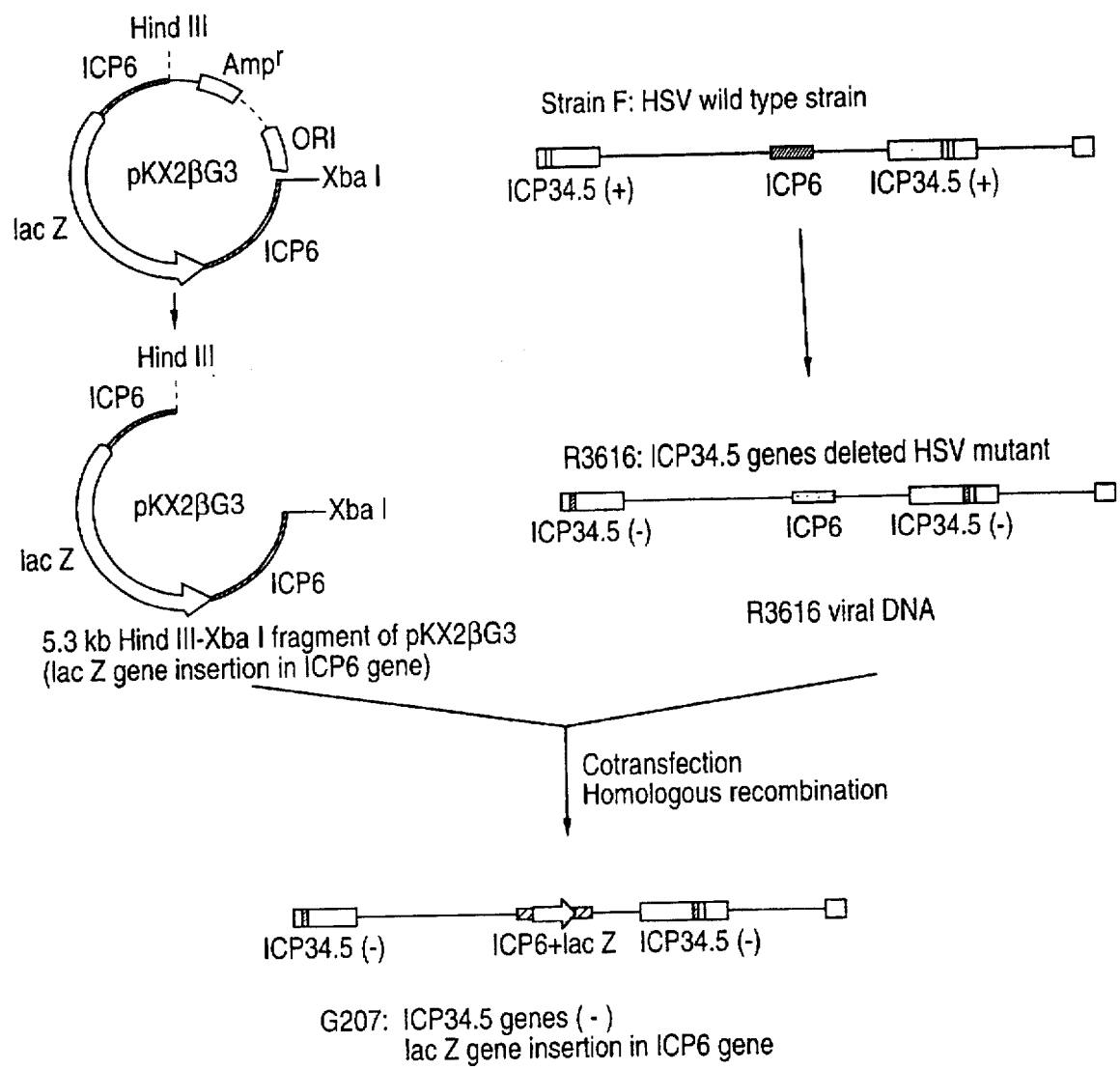
FIG. 4 is a schematic illustration of the construction of a mutant herpes simplex virus containing a 1 kB deletion in both copies of the γ34.5 gene and an insertion in the ICP6 gene.

An exemplary mutant herpes simplex virus vector of the instant invention can be constructed by homologous recombination using DNA isolated from R3616 virus and a 5.3 kB HindIII-XbaI fragment of pKX2-βG3. One example of such a mutant within the present invention is designated "G207." FIG. 4 illustrates the construction of G207. Five isolates were purified and termed G207–1, –2, –3, –4, –5.

The HSV-1 mutant R3616, derived from HSV-1 wild-type strain F, contains a 1-kB deletion in both copies of the γ34.5 gene. To construct an ICP6 lacZ insertion in R3616 viral DNA, the 5.3 kb HindIII-XbaI fragment of pKX2-βG3, which contains a lacZ insertion in the 2.3-kB XhoI fragment of ICP6 gene, was cotransfected with R3616 infectious viral DNA into Rabbit Skin (RS) cells, and introduced into the viral DNA by homologous recombination. Plasmid pKX2-βG3 containing a lacZ gene insertion in the 2.3 Kb XhoI fragment of ICP6 gene (KOS), was kindly provided by Dr. S. K. Weller (Univ. of Connecticut). Goldstein and Weller, *J. Virol.* 62: 196 (1988). Plasmid pKpX2' was constructed by partial digestion of pKX2-βG3 with BamHI, removal of lacZ gene and religation. Plasmid pRB4081 containing NcoI-SphI fragment of γ34.5 gene, was kindly provided by B. Roizman. Chou et al., *Science* 25: 1262 (1990). All recombinant plasmids were propagated by standard procedures. All plasmids and viruses can be constructed with available materials in view of the present application.

Two hundred to 1,000 infectious units of R3616 viral DNA (approximately 1 μg) are co-transfected with a 10-fold molar excess of the 5.3 kB insert of pKX2-βG3, which is excised by cutting with XbaI and HindIII, to RS cells. When wide spread cytopathic effects were observed, progeny are harvested and titers determined on Vero cells.

On day 2 or 3 following infection, plaques were stained with X-gal solution. Recombinant viruses were identified by plaques staining positive with X-gal. Recombinant viral plaques (γ34.5-/ICp6- and LacZ+) stain blue in the presence of X-gal. Recombinant virus from blue plaques is purified and the DNA analyzed by restriction endonuclease mapping to confirm the DNA structure of the mutant viruses. Blue plaques were purified three times by passage in Vero cells in a limiting dilution method before stocks were made.

The plaque morphology of G207-1 and G207-2 was analyzed as well as the effect of various concentrations of IFCS-containing medium on plaque morphology. Infected vero cell monolayers were cultured at 37° C. in medium containing 0.5%, 1%, 2.5% and 5% IFCS; were fixed at 36–48 hr post-infection; and were stained with X-gal, to detect β-gal activity, and then counterstained with neutral red.

G207-1 mutants produced non-syncytial plaques, whereas G207-2 mutants produced syncytial plaques, characterized by extensive cell-cell fusion.

Table 4 documents the increasing plaque diameters under conditions of increased cell growth for G207-1 and G207-2. The diameters of plaques were measured using a micrometer under an inverted phase-contrast microscope at 40X magnification. Each value represents the average diameter of 15 plaques.

TABLE 4

Diameters of plaques in various concentrations of IFCS medium

| | 0.5% IFCS | 1% IFCS | 5% IFCS |
|---|---|---|---|
| R3616 | 0.48 ± 0.13 | 0.44 ± 0.12 | 0.45 ± 0.094 (NS) |
| | | | 1.1 ± 0.36 (Syn) |
| G207-1 (Non-syn.) | 0.42 ± 0.15 | 0.48 ± 0.16 | 0.63 ± 0.18 |
| G207-2 (Syn.) | 0.45 ± 0.16 | 0.48 ± 0.17 | 1.0 ± 0.30 |

(mm: mean ± SD)

Figure 5:
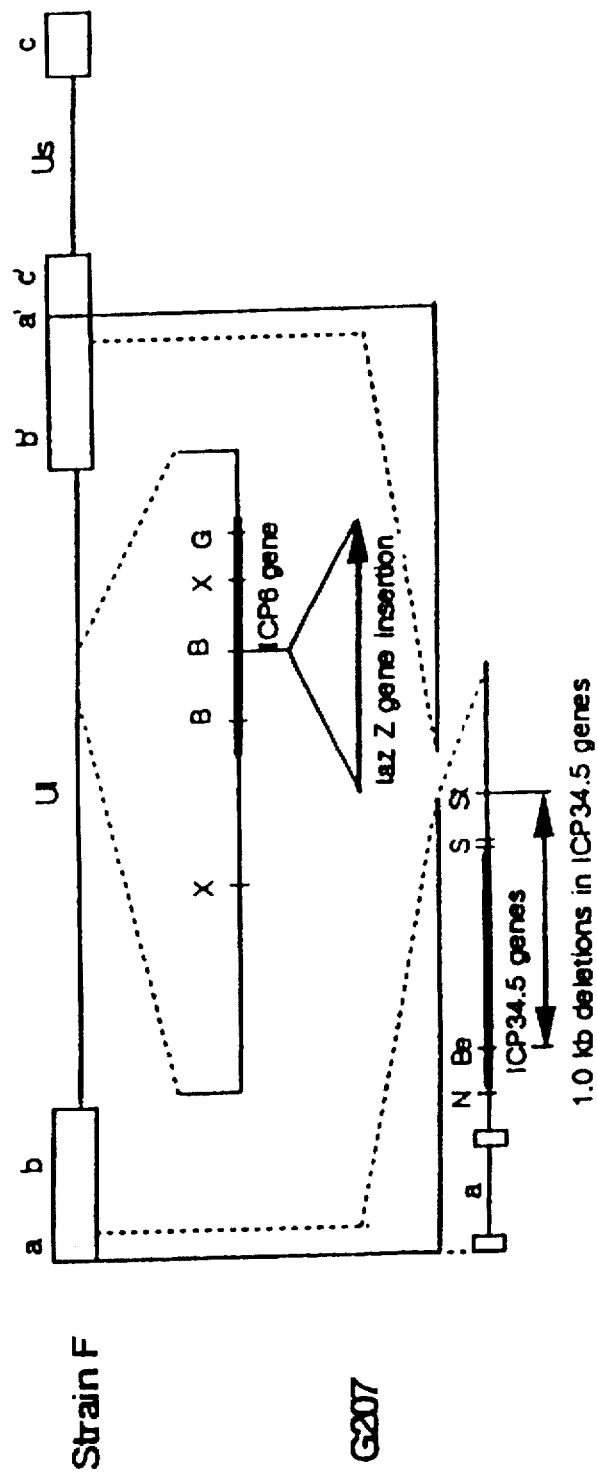
FIG. 5 shows the sequence arrangement of a mutant herpes simplex virus, G207-1, compared to its parental wild-type background (strain F). The abbreviations are B, BamHI; Be, BstEII; G, BglIII; N, NcoI; S, ScaI; St, StuI; and X, XhoI.

The sequence and gene arrangement of G207 viruses compared to its strain F wild-type background is illustrated in FIG. 5. The boxes on the top line of FIG. 5 represent the inverted repeat sequence flanking the long ($U_L$) and short (Us) components of herpes simplex virus genome, which is represented by thin lines. The expanded domains of the long unique region show the location of the ICP6 gene. The thick line shows the transcribed sequences of ICP6 gene. Mutant G207 contains the structural gene of lacZ inserted into the BamHI site in the ICP6 gene. The expanded domains of the repeat regions show the location of the γ34.5 gene. Mutant G207 contains a 1 kB deletion in both copies of the γ34.5 gene.

Analysis of Mutant Viral DNA

In order to confirm the correctly altered structure of the herpes simplex virus vectors, Southern blot analysis was performed on the mutants of invention. Viral DNAs were prepared from partially purified virions. Total viral DNAs (KOS, hrR3, Strain F, R3616, and G207) were digested with restriction endonuclease, separated by agarose gel electrophoresis in a Tris-borate-EDTA buffer and transferred by the method of Southern. Recombinant DNAs used as probes for hybridization were labeled by ECL labeling Kit (Amersham) as suggested by the supplier. To confirm that the viral mutants contain the lacZ gene at the appropriate position, total DNA was digested with Xho I and subjected Southern blot hybridization in duplicate. Filters were hybridized with labeled pkpX2', which contains wild-type sequences of ICP6 gene. HSV-1 wild-type KOS contains a wild-type 2.3 kB Xho I fragment, whereas, hrR3 (KOS derived and lacZ insertion mutant in ICP6 gene) contains the 5.3 kB fragment expected if the lacZ gene was inserted. HSV-1 strain F contains an approximately 6.0 kB Xho I fragment due to a polymorphism between herpes simplex virus wild-type strains. G207 contains a 9.0 kB fragment, expected if the lac Z gene was inserted into the 6.0 kB fragment of strain F. When the filter was hybridized with a lacZ gene probe alone, only the 5.3 kB fragment of hrR3 and the 9.0 kB fragment of G207 was detected. These results demonstrate that the lac Z gene fragment is inserted into appropriate site in the genome.

To confirm that G207 contains deletions in the γ34.5 gene. Viral DNAs of strain F, R3616, G207 were digested with Bam HI and subjected to Southern blot hybridization. Plasmid pRB4081, containing wild-type sequences of the γ34.5 gene was used as probe. The γ34.5 gene maps in the Bam HI SP and S fragments. Strain F contains the wild-type Bam HI SP and S versions of these fragments, whereas R3616 and G207 contain the deleted versions of these fragments. These results demonstrate that both γ34.5 genes are deleted in R3616 and G207 viral DNA.

Herpes Simplex Virus Mutants Targeted to Specific Cell Types

Plasmids containing the 2.2-kB EGFR promoter fragment from pERCAT2, see Johnson et al., *J. Biol. Chem.* 263: 5693 (1988), and a 2.1-kB BFGF promoter fragment from pF2.ICAT, see Shibata et al., *Growth Factor* 4: 277 (1991), are used to characterize transient expression of a marker protein (β-galactosidase). The cell-specificity of these constructs is confirmed in human U-87MG glioblastoma cells for BFGF [Takahashi et al., *FEBS Letters* 288:65 (1991)] and in A431 human epidermoid carcinoma cells for EGFR. Liberman et al., *Nature* 313:144 (1985). A431 cells are available as ATCC: CRL 1555; U-87MG MG cells are available as ATCC: HTB 14.

For example, the tumor cell-specific promoter is cloned into an ICP 4 plasmid upstream of the ICP4 coding region. Examples of ICP4 plasmids include pGH108 or pXhoI-C. Roberts et al., *J. Virol.* 62: 4307 (1988). This plasmid is then recombined into herpes simplex virus ICP4$^-$. Herpes simplex virus ICP$^-$ can be constructed by deletions or insertions into the ICP4 coding region. DeLuca et al., *J. Virol.* 56: 558 (1985); DeLuca and Schaffer, *Nucleic Acids Res.* 15: 4491 (1987); Paterson and Everett, *J. Gen. Virol.* 71: 1775 (1990). The vector of the invention can also be made ICP4− by a deletion or insertion into the ICP4 coding region. Such ICP4− vectors are isolated on ICP4 expressing cells. DeLuca et al., supra; DeLuca and Schaffer, supra; Paterson and Everett, supra. Alternatively, the ICP4 regulatory region of the herpes simplex virus vector is replaced with the tumor-specific promoter so that ICP4 is only produced in cells capable of expressing the replaced promoter. The herpes simplex virus mutant containing its ICP4 gene under the control of a tumor-specific promoter is tested for its ability to infect and kill specific tumor cells.

EXAMPLE 2

SAFETY AND EFFICACY STUDIES

The in vitro efficacy of the mutants as anti-glioma agents can be determined using assays of glioma cytotoxicity on cultures of a long-term human glioma cell line, U-87MG, as well as early-passage human glioblastomas. To evaluate tumor inhibition in vivo, subcutaneous U-87MG xenografts in nude mice are treated separately with inoculations of each viral mutant or vehicle, and tumor growth rates were analyzed. To investigate the potential effects of the herpes simplex virus mutant treatment on survival, nude mice with intracranial U-87MG xenografts are treated with virus or vehicle inoculations, and overall survival is compared.

To evaluate the degree of tumor eradication, as well as the potentially retained neurovirulence of the viruses when used at doses necessary to achieve prolonged survival, the brains of long-term survivors with intracranial xenografts are sectioned, stained, and microscopically examined. For effective in vivo tumor inhibition and survival prolongation, careful choice of mutant employing the assays described herein is essential. The following methods provide clear guidance to those of skill in the art to screen for mutant viral vectors that are effective in vivo in inhibiting tumor growth and prolonging survival. To establish the relative safety of these viruses as potential anti-glioma agents, their susceptibility to the common antiherpetic agent ganciclovir is investigated. Finally, to establish the safety of intracerebral inoculation of the mutant viral vector, animals receive an intracerebral inoculum of the mutant virus and are subsequently assessed for encephalitis.

In vitro Cytopathic Killing

The ability of the herpes simplex virus vectors of the invention to kill tumor cells is first tested in cell culture. All viral work is done in approved, designated viral vector rooms. Viruses are initially grown on Vero cells, as described in Martuza et al., *Science* 252:854 (1991). To maximize the titer of the viral mutant, the initial viral suspension was centrifuged at 34,500 g for 2 h at 4° C., and the pellet was subsequently suspended in media and again tittered. Viruses are applied at varying multiplicities of infection (MOIs), between $10^1$ and $10^{-4}$. MOI values were calculated from cell number. The appropriate number of viral pfu was applied and distributed evenly. Coen et al., *J. Virol.* 53: 477 (1985). All viral-infected cell cultures were compared with control cultures (DMEM+ only, no virus). Cells were maintained and observed microscopically. Cells that had become rounded, losing normal morphology, and those lifting from the plate were considered dead. Monolayers were considered completely destroyed when 99% or more of the cells exhibited such cytopathic effects.

Either the mutant or its wild-type parent were applied to a human glioma line (U-87MG) and African green monkey kidney (Vero) cells at multiplicities of infection (MOIs) from $10^{-4}$ to $10^1$ in DME+ (Dulbecco's modified Eagle's medium with 1–5% heat-inactivated fetal calf serum (IFCS) and antibiotics). The malignant human glioma line U-87MG was obtained from American Tissue Cell Collection, Rockville, Md. Additionally, two primary human malignant gliomas were obtained as surgical tumor specimens. Martuza et al., supra, (1991). All cells were grown in Dulbecco's modified Eagle's medium with 10% fetal bovine serum and antibiotics (DMEM+).

Subconfluent monolayers of U-87MG and Vero cells were infected with the mutant viral vectors of the invention at varying MOIs. The infected cells are cultured in 1–5% IFCS-containing medium at 34.5° C. The viable cells were identified by the Trypan blue exclusion method. The mutant expressing cytopathic effects at 24 hours that is proportional to the MOI and expressing >99% cytopathic effect after 10 days in U-87MG is deemed to possess the ability to kill glioma cells in vitro. The lowest inoculum of the mutant virus that can sustain a spreading infection to destroy the entire monolayer of U-87MG cells will provide one of the doses at which the mutant is evaluated in vivo. The mutant viral vector also is tested against a different human glioma line (T98G) at various MOIs and assessed for its ability to produce monolayer destruction within 10 days.

Short-term glioma cultures were established by explanting three malignant human gliomas (one anaplastic astrocytoma and two glioblastomas) obtained at surgery in DME+ and were studied at the second passage. The mutants are tested at various MOIs for their cytopathic effects. The herpes simplex virus mutant and dose that is cytopathic in all three primary malignant gliomas is deemed to be able to kill a wide variety of human brain tumor cells in vitro.

In addition to glioma cultures, the viral mutants are tested for their ability to kill 3 human malignant meningiomas, 1 atypical meningioma, 5 neurofibrosarcomas, and 2 medulloblastomas in cell culture, and in the in vivo models. The viral mutants are tested at MOIs ranging from $10^1$ to $10^{-4}$. Significant tumor inhibition by the mutant virus reveals a wide range of nervous system tumors for which the viral mutant is efficacious in killing human brain tumor cells.

Figure 6:
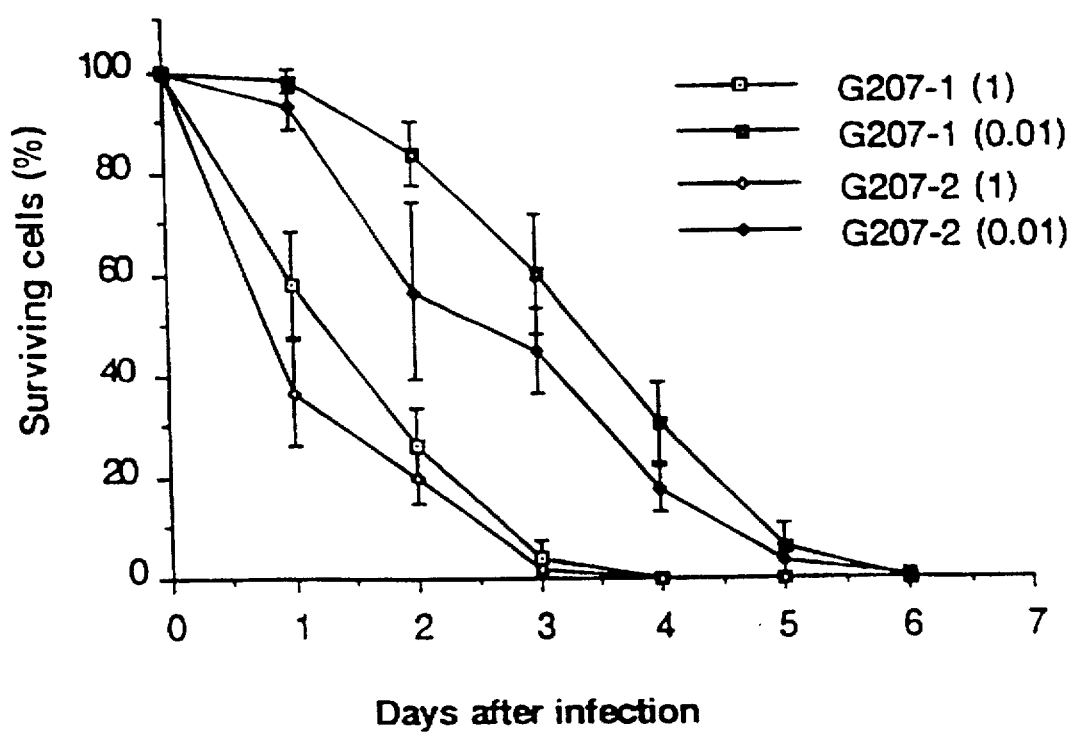
FIG. 6 is a graph illustrating the ability of G207-1 and G207-2 to kill all human U-87MG glioma cells in culture, including at low multiplicity of infection (MOI=0.01).

FIG. 6 documents the in vitro cytopathic efficacy of G207-1 and G207-2 on U-87MG cells. Subconfluent monolayers of U-87MG cells were infected with G207-1 or G207-2 (MOI=0.01 or 1), while the controls were mock-infected and cultured with 10% IFCS-containing medium at 34.5° C. The viable cells were identified by the Trypan blue exclusion method. The number of surviving cells relative to the number of cells in mock-infected control cultures (100%) was assessed. Each data point represents the mean of triplicates. Vertical bars indicate the standard deviation of the triplicates. Each of the viral mutants killed all of the tumor cells by 6 days post-infection. Cytopathic effect appeared on day 1 postinfection for MOI of 1.0, with >99% cytotoxicity evident by day 3 for 1.0 MOI and by day 6 for 0.01 MOI. The cytopathic efficacy of these mutants can also be tested on the human glioma cells lines T98G, U-138MG and A172.

The herpes simplex virus vector of the instant invention can be used to mediate the destruction of other human tumors. Examples of other human tumors that may be amenable to this invention include melanoma, carcinoma of the prostate, breast cancer, pancreatic cancer, lung cancer, colon cancer, lymphoma, hepatoma, and mesothelioma. Human tumor cells can be cultured from primary tumors as described. Fogh and Trempe, HUMAN TUMOR CELLS IN VITRO, Plenum Press, New York (1975) p. 115; Wilson, chapter 8, ANIMAL CELL CULTURE, A PRACTICAL APPROACH. IRL Press (1986). Human melanoma cell line, SK-MEL-31 (ATCC: HTB 73); human prostate carcinoma cell lines, Du145 (ATCC: HTB 81) and PC3 (ATCC: CRL 1435); human epidermoid carcinoma cells, A431 (ATCC: CRL 1555); and human lung carcinoma cells, Calu-1 (ATCC: HTB54) are susceptible to infection by attenuated mutants of HSV-1.

Anti-viral Agent Sensitivity

To overcome the insensitivity of some of the prior art herpes simplex virus mutants to anti-viral agents, another drug target (for example, suicide-gene) is inserted into the virus. For example, the CMVUL97 gene (gan$^r$; pGMT7-UL97) is inserted into TK$^-$ HSV-1 mutants and tested for its ability to complement the inability of TK$^-$ HSV-1 to replicate in serum-starved cells and confer ganciclovir sensitivity on this recombinant. After the viral vector containing the suicide gene is tested for ganciclovir sensitivity, a comparison of the ED$_{50}$ (in vitro) and Mean Survival Time of the suicide containing and suicide absent viral vectors (e.g., HSV-1 mutants TK$^{-/UL}$97 and dlsptk) is made in the presence of ganciclovir.

Ganciclovir-sensitivity assay

Figure 7:
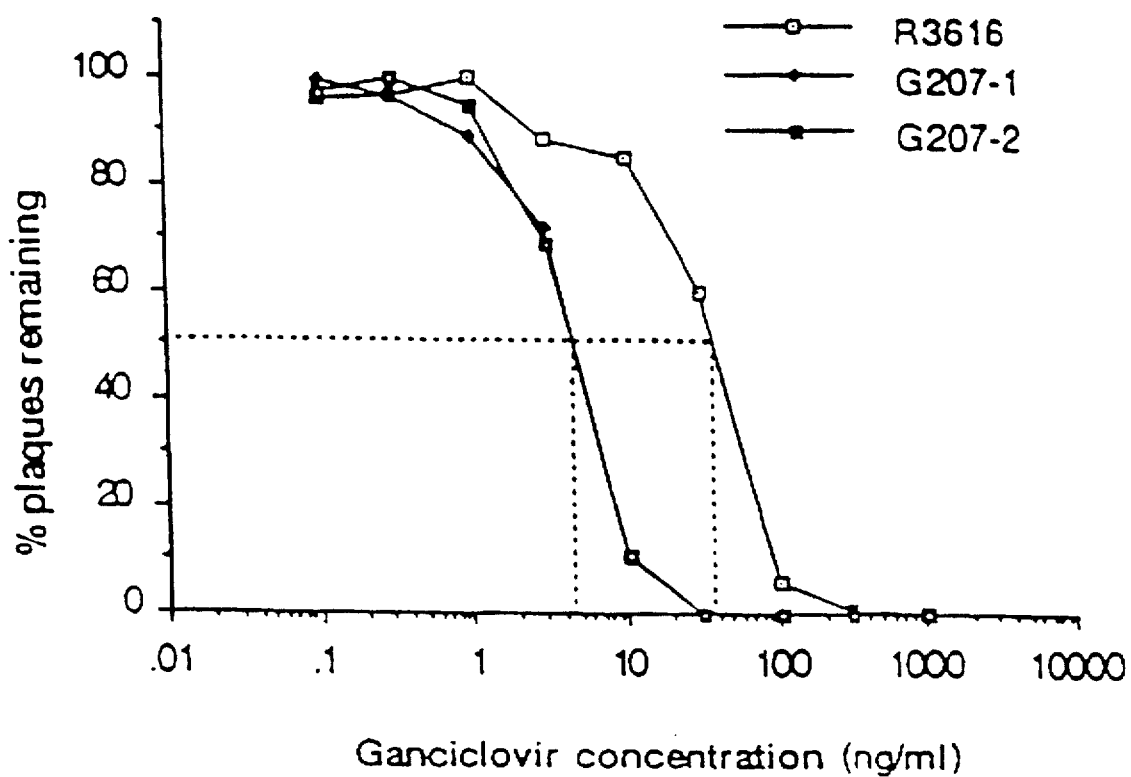
FIG. 7 is a graph illustrating the ganciclovir (GCV) sensitivity of R3616, G207-1, and G207-2 which reveals that G207-1 and G207-2 are ten-times more sensitive to ganciclovir than R3616. R3616 (strain F) has the same sensitivity to ganciclovir as strain KOS (wild-type).

Confluent monolayers of Vero cells in 12-well plates are infected with 100 pfu of R3616 or G207, where the MOI remains below 0.0005. After removing the virus inoculum, DMEM plus 1% inactivated fetal calf serum and 1000-fold diluted human immunoglobulin (Armour Pharmaceutical Company; Kankakee, Ill.) containing various concentrations of ganciclovir is added to triplicate cultures and cells are incubated at 37° C. Plaques are visualized by Giemsa stain and counted on day 3 post infection. The ganciclovir (GCV) sensitivity of R3616, G207-1, and G207-2 is illustrated in FIG. 7, which reveals that G207-1 and G207-2 are ten times more sensitive to ganciclovir than R3616. The ganciclovir sensitivity of R3616 is similar to wild-type. Each data point represents the mean of triplicates. The plaque number in the absence of ganciclovir represents 100% plaques. The dotted line indicates the ED$_{50}$.

Temperature sensitivity of mutant viral vector

To provide an additional safety feature that further compromises viral replication in the presence of encephalitis and fever, the sensitivity of the mutant viral vectors to temperatures greater than the basal temperature of the host are ascertained. Table 5 demonstrates the decreased plaquing efficiency of G207-1 and G207-2 at elevated temperatures. The plaque efficiencies were determined by titering virus stocks on Vero cell monolayers. Infected Vero cell monolayers are cultured with 1% IFCS medium at 37° C. or 39.5° C. and fixed at 48 hr postinfection. Plaques are counted following Giemsa staining. Titers are expressed as pfu/ml. The hrR3 mutant showed temperature sensitivity compared to the parental strain KOS as previously reported. Goldstein and Weller, Virology 166:41 (1988). The HSV-1 wild-type strain F, which is the parental strain of R3616, G207-1, and G207-2, also is temperature sensitive. The R3616, G207-1, and G207-2 mutants remain as temperature sensitive as their parental strains.

TABLE 5

Plaquing Efficiencies of KOS, hrR3, R3616, G207-1, and G207-2 on Vero Cells at 37° C. and 39.5° C.

| Virus | 37° C. | 39.5° C. |
|---|---|---|
| KOS | 1.6 × 10$^7$ | 6.6 × 10$^6$ |
| hrR3 | 3.6 × 10$^8$ | <10$^4$ |
| R3616 | 1.2 × 10$^9$ | <10$^5$ |
| G207-1 | 6.0 × 10$^7$ | <10$^4$ |
| G207-2 | 6.0 × 10$^7$ | <10$^4$ |

EXAMPLE 3

IN VIVO EXTRACRANIAL MODELS

Subcutaneous glioma xenograft transplantation and therapy

The effects of mutant herpes simplex virus infection on human brain tumors in vivo were assessed in athymic mice to allow for growth of the human tumors. Subcutaneous xenograft implantation was performed as previously described. Martuza et al., Science 252:854 (1991) and Markert et. al., Neurosurg. 32:597 (1993). To test the effect of the herpes simplex virus mutants on human glioma in vivo, 1 mm$^3$ minced glioma pieces (obtained from nude mice previously injected subcutaneously with cultured U-87MG cells) are implanted subcutaneously into nude mice. Nude mice are anesthetized with 0.25 ml of a solution consisting of 84% bacteriostatic saline, 10% sodium pentobarbitol (1 mg/ml), and 6% ethyl alcohol. Animals dying within 48 hours of any procedure are considered perioperative deaths and are excluded from analysis. Deaths in the subcutaneous tumor experiments are excluded from analysis (no significant difference in deaths occurred between virus-treated groups and their corresponding controls).

Between weeks 4 and 5, animals growing tumors ($\leq$8 mm in diameter) are divided into two groups of 7 to 10 animals per group. Controls received intraneoplastic injections of 50 or 60 µl of DMEM+; treated animals received similar intraneoplastic injections of virus suspended in DMEM+. Doses administered for each virus vary between 10$^6$ and 10$^8$ plaque forming units. Care is taken to distribute virus throughout the tumor. For two-dose experiments, subsequent injections of DMEM+ or virus are made on Day 14. Similar experiments are conducted for each of the virus mutants at various doses.

Tumors were measured weekly or twice weekly with Vernier calipers. Growth of subcutaneous xenografts was recorded as the tumor growth ratio by formula ([1×w×h]/2)

/([1×w×h]$_{day\,0}$/2) as described in Martuza et al., supra (1991). Growth ratio comparisons were made at 28 days after the initial treatment. Potential differences in growth ratios were assessed by use of the one-sided Wilcoxon rank test.

Subcutaneous glioma xenograft therapy using G207

Mice harboring subcutaneous tumors (approximately 6 mm in diameter) were randomly divided (n=6 per group) and treated intraneoplastically with either $5 \times 10^7$ pfu of G207 virus suspended in 0.05 ml virus buffer or with buffer alone. The tumor diameter was measured by external caliper measurements. For pathological studies, tumor-bearing mice (>10 mm in diameter) were treated with $1 \times 10^7$ pfu of G207 and sacrificed on day 8, 15 postinjection. Tumors were removed, placed in fixative for 1 hr and submerged in cold phosphate buffered saline. Tumors were then placed overnight in X-gal solution.

Figure 8:
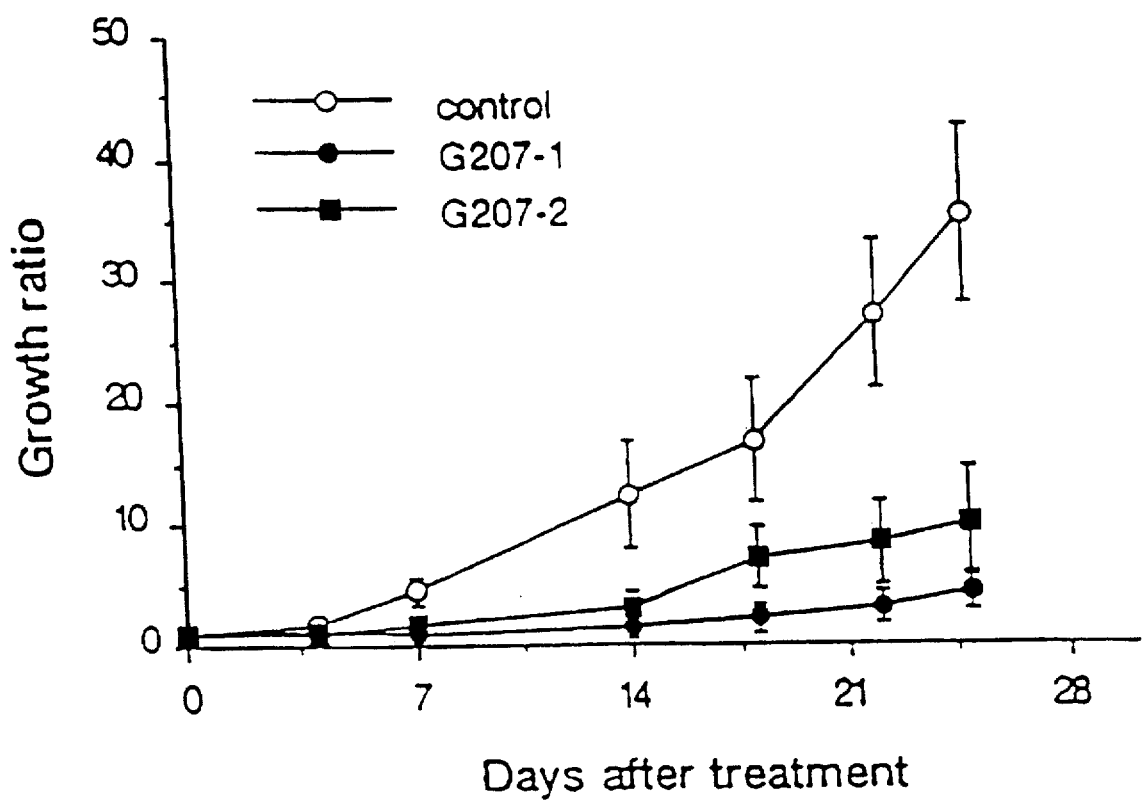
FIG. 8 is a graph illustrating the ability of G207-1 and G207-2 to inhibit the growth of human brain tumor cells (U-87MG) in the subcutaneous human brain tumor model in athymic mice.

FIG. 8 is a graph showing the growth ratio of subcutaneous U-87MG tumors in Balb/c (nu/nu) mice treated with $5 \times 10^7$ pfu of G207-1 (closed circle) or G207-2 (closed square) on Day 0, or with control medium alone (open circle). Tumors were measured twice weekly with calipers and the growth ratio calculated by dividing the tumor volume by the tumor volume on the day of initial inoculation. Bars represent mean±SE for each group. The mean tumor growth rate was significantly inhibited in tumors treated with G207 compared to control tumors treated with medium alone.

Subrenal Capsule Model

The effects of G207 on U-87MG cells grown in the subrenal capsule of the nude mouse also would be tested because the subrenal capsule is a site used for monitoring growth of other nervous system tumors. Lee et al., *Neurosurg.* 26: 598 (1990); Medhkour et al., *J. Neurosurg.* 71: 545 (1989). U-87MG cells ($1.5 \times 10^6$) would be implanted in the subrenal capsule of nude mice. Ten days later, the tumors are measured and inoculated with varying pfus of G207 in 1 µl DME+ or 1 µl DME+ alone. All mice were re-examined at 14 days and 26 days following inoculation to measure tumor size. Virus-treated tumors that are smaller than control tumors show that the mutant virus is capable of killing tumor cells in vivo.

EXAMPLE 4

IN VIVO INTRACRANIAL TUMOR KILLING

To evaluate the in vivo efficacy of the replication-competent herpes simplex virus vector in treating intracerebral gliomas, nude mice would be stereotactically inoculated in the right frontal lobe with $1.6 \times 10^5$ U-87MG cells. In a pilot study, a similar cell inoculum caused 100% mortality within 1.5 months.

Ten days after tumor implantation, animals would be divided randomly into treatment groups to receive the following therapies at the same stereotactic coordinates used for the tumor implants: (1) the control group would receive intracranial inoculations of 6 µl DME+ as above, (2) the second group would receive intracranial inoculations of $10^3$ pfu (low-dose) of the mutant replication-competent viral vector, (3) the third group would receive intracranial inoculations of $10^5$ pfu (middle-dose) of the test virus, and (4) the fourth group would receive intracranial inoculations of $10^7$ pfu (high dose of the test virus), each suspended in 6 µl DME+. Inoculations would be in 2 µl DME+ at the stereotactic co-ordinates initially used to inject the U-87MG cells. By 7 weeks, all control animals would be dead, as they have been in past evaluations. A mutant viral vector of the instant invention is one that kills intracerebral brain tumors by keeping a significant number of the mice alive by seven weeks post-treatment. Significance is determined by plotting experimentals vs. controls in a one-tailed Fischer exact test.

In vivo Neuropathology

The animals that remain healthy and neurologically normal at 19 weeks are sacrificed. The entire brain will be fixed, serially sectioned at 7 µm intervals, stained with hematoxylin and eosin, and microscopically examined for evidence of encephalitis and/or tumor. The absence of evidence of encephalitis would reveal that the viral vector possesses the characteristic of decreased or attenuated generalized neurovirulence. The absence of evidence of tumor would reveal that the viral vector is efficacious in killing human brain tumor cells in vivo.

In vivo treatment would be more effective for those herpes simplex virus mutants that exhibit decreased neurovirulence yet retain cytopathic effects in glioma cells because such vectors would allow tumor treatment at higher viral doses.

Studies of Herpes Simplex Virus Mutants in Immune Competent Animal Models

To test the efficacy of the herpes simplex virus mutants in killing human tumor cells in the presence of a competent immune system, the GL261 mouse ependymoblastoma model would be utilized in its syngeneic host, the C57BL/6 mouse. The GL261 cell line would be implanted subcutaneously or intracranially in C57BL/6 mice. Animals harboring subcutaneous GL261 tumors would be randomly divided and treated intraneoplastically as described above in the nude mouse model. The virus-treated group showing significant growth inhibition, as assessed by the Wilcoxon rank sum test would then be assayed in the intracranial studies.

For intracranial studies, mice would be injected with $10^4$ GL261 cells in the right frontal lobe. After 7 days, the animals would be inoculated intraneoplastically with either mutant virus or with medium alone. All of the media treated mice would probably die, as they have in previous studies. The viral mutants that would be capable of prolonging mouse survival to 40 days or longer after tumor cell implantation would be considered efficacious in killing human brain tumor cells in vivo.

Neuropathology and Tumor Killing in Herp Simplex Virus-Immunized Animals

Since herpes simplex virus is endemic in society, an effective therapy would have to accommodate patients that have been exposed to HSV-1. Accordingly, it is important to determine whether the mutant herpes simplex virus vectors of the present invention can destroy tumor cells in situ in animals that have been previously immunized to herpes simplex virus. The effect of herpes simplex virus-immunization on the ability of the mutant viral vector to kill tumor cells in vivo would be tested in the GL261 intracranial model in C57BL/6 mice.

C57BL/6 mice would be immunized against the KOS strain of herpes simplex virus; another group of mice would be immunized with the wild-type strain from which the vector is derived; another group would be mock-immunized with saline. Those mice that demonstrate high serum titers of antibody by plaque reduction assay 2 weeks after inoculation would be used as herpes simplex virus-immunized animals. Four weeks after immunization, tumor cells would be injected intracerebrally as described above. One week later, the tumor would be inoculated at the same stereotactic coordinates with the vector using medium alone in the negative control group. The effect of pre-immunization on tumor cell growth, subsequent animal death, and the ability of herpes simplex virus to kill the tumor cells would be assessed as described for the intracerebral model.

In addition, several animals from each group would be sacrificed for a neuropathological study during each of the acute phase (2 days), subacute phase (1 week), and chronic phase (1 month and 3 months). The following histologic pathologies would be assessed: tumor size, immune cell infiltration, brain edema, necrosis, alteration of neurons, glia, myelination, hemorrhage, blood vessel proliferation or destruction, reactive astrocytes, normal neurons and glia, ischaemia, gliosis and the spread of virus (PCR for viral DNA or β-galactosidase). These studies would determine whether pre-immunization against herpes simplex virus has any effect on the mutant viral vector's ability to kill tumor cells or elicit neuropathogenesis.

Identification of Virus Location

Herpes simplex virus containing the *E. coli* LacZ gene and expressing β-galactosidase after viral infection is a useful marker for histologically determining the dynamics and spread of the tagged virus. Because the hrR3 mutant contains the *E. coli* LacZ gene inserted into the ICP6 gene such that the virus expresses β-galactosidase during viral replication, infected cells can be stained with X-gal. Goldstein and Weller, supra (1988).

This marker permits following the spread of virus in vivo by examining brain specimens from mice at various time points after infection with hrR3 by staining with X-gal. Kaplitt et al., *Mol. & Cell. Neurosci.* 2: 320 (1991). The presence of virally-infected cells in fixed brain sections is determined by PCR and compared to the proportion of X-gal staining cells. The tumor is visible after counter-staining with H&E or immunohistochemically with tumor-cell or species-specific markers. In this way, replication-competent viral vectors would be tracked and assessed for their ability to spread to tumor cell deposits at a distance from the main tumor mass. Histologic studies would determine the maximum distance that the virus can spread to reach a distant tumor deposit.

Another sensitive technique for identifying the presence of herpes simplex virus or defective herpes simplex virus vector in brain sections would employ PCR. In order to localize viral DNA, DNA for PCR would be isolated from cells after fixation and histochemistry such that even single positive cells would generate a specific PCR signal. Using specific oligonucleotide primers, unique PCR products would be generated from the viral vector DNA present in these cells. Cover slips would be removed from slides and small pieces of tissue would be dissected out. The tissue would be incubated with proteinase K, Tween-20, oligonucleotides and PCR buffer at 65° C. for 90 min. and then increased to 95° C. to inactivate proteinase K. The treated samples would be diluted with dNTPs, PCR buffer and Taq DNA polymerase and thermocycled. The PCR products then would be size analyzed by agarose gel electrophoresis. In addition, available in situ PCR techniques could be utilized to localize viral DNA during the neuropathological studies. Embretson et al., *Proc. Nat'l Acad. Sci. USA* 90: 357 (1993).

Safety of Replication-Competent Herpes Simplex Virus Mutants in Mice and Non-human Primates To establish that the herpes simplex virus vector does not produce neurovirulence at the dose required to kill tumor cells, animals receive inoculations of tumor-killing doses of the mutant herpes simplex virus vector to determine whether the vector would cause herpes simplex virus encephalitis in vivo. Aliquots (10 μl) of G-207-1, G-207-2 and strain F were inoculated into the right cerebral hemisphere of three week old mice; deaths were scored up to 21 days postinfection. Table 6 shows that the intracerebral inoculation of Balb/c mice with the parent wild-type virus (strain F) at $10^3$ p.f.u. caused half the animals to die from encephalitis. Chou et al., *Science* 250: 1262 (1990). The known LD50 for strain 17 is also $10^3$ p.f.u.'s. McKie et al., *J. Gen. Virol.*, 75: 733 (1994). In contrast, no mortality or illness was observed following intracerebral inoculation of the highest titers of G207-1 or G207-2 that we could produce ($10^7$ p.f.u. in 10 ul). The dose of $10^7$ p.f.u. was shown to kill tumor cells in vivo in the subcutaneous U-87MG tumor growth model, as shown in FIG. 8.

TABLE 6

Neurovirulence of G207-1 and G207-2 in Balb/c mice
(i.c. injection for $LD_{50}$)
Balb/c mice (3 wks old)
intracranial injection (10 μl)

| | | |
|---|---|---|
| G207-1 | $1 \times 10^7$ pfu/10 μl | × 8 (8/8, all mice alive) |
| G207-2 | $1 \times 10^7$ pfu/10 μl | × 8 (8/8, all mice alive) |
| Strain F | $1 \times 10^3$ pfu/10 μl | × 8 (4/8, 2 died day 3, 1 died on day 5, 1 died on day 14) |

*Aotus trivigatus*, a primate species exceedingly sensitive to herpes simplex virus encephalitis, is used to test the safety of the mutant herpes simplex virus vectors of the invention. Katzin et al, *Proc. Soc. Exp Biol. Med.* 125: 391 (1967); Melendez et al., *Lab. Anim. Care* 19: 38 (1969).

Magnetic Resonance Imaging (MRI) scanning or other imaging analysis would be used to assess encephalitis. Monkeys would receive a brain MRI with and without gadolinium prior to the start of the trial.

Initial testing would be performed at the highest dose that can be generated for the particular mutant that has been determined to be safe in mice ($LD_{10}$ or less). For example, $10^7$ pfu would be administered intracerebrally for the G207 deletion mutant to be tested. The dose that is well tolerated by a species known to be highly sensitive to herpes simplex virus, provides the most compelling evidence that this treatment would be reasonably safe in humans. If no clinical or MRI evidence of encephalitis is noted within 1 month, another animal would be tested at that same dose or at a log higher. The animal would be observed daily for signs of neurological and systemic illness.

This method can determine the maximal dose that can safely be administered intracranially without producing death, persistent neurological signs, or progressive illness. After 12 months, the animals would be sacrificed and the brains examined for loss or alteration of neurons, glial reaction, myelination, hemorrhage, blood vessel proliferation or destruction, viral DNA (by PCR) or virally-induced β-galactosidase in blood vessels, ischaemia, necrosis, gliosis, and inflammatory reaction. These studies would elucidate the neuropathologic lesions (if any) that might be expected to occur in the normal primate brain as a result of infection with this vector.

The genus Aotus had been long thought to be a monotypic genus with *Aotus trivigatus* as its sole representative. Studies have proved, however, that Aotus is a multispecific genus with species and subspecies ranging in chromosome number from 2n=46 to 2n=56 (*Aotus nancymai*, karyotype 1 owl monkey, 2n=54). When the susceptibility of owl monkeys to herpes simplex virus was reported in the 1960's, they could not distinguish *Aotus trivigatus* from *Aotus nancymai*. Malaga et al., *Lab. Anim. Sci.* 41: 143–45 (1991). Under current taxonomic classification, however, *Aotus nancymai* was formerly believed to represent *Aotus trivigatus*. Hershkovitz, *Amer. J. Primatol.* 4:209 (1983).

Replication-competent viral vectors of the instant invention would be tested for their ability to produce herpes simplex virus encephalitis in primates that are sensitive to herpes simplex virus induced encephalitis, namely, Aotus nancymai and/or Aotus trivigatus. An Aotus nancymai is still living three weeks after being inoculated with $10^7$ pfu of the G207 mutant.

EXAMPLE 5

TREATMENT OF HUMAN BRAIN TUMORS WITH REPLICATION-COMPETENT VIRAL VECTORS

Patients with recurrent glioblastoma that was refractory to standard surgery, radiotherapy and chemotherapy would be treated with herpes simplex virus therapy. The patient would be scanned using MRI or CT or other technique and the tumor and normal brain registered in stereotactic space. The virus would be administered using stereotactically guided neurosurgical techniques. A computer tomography (CT) scan or magnetic resonance imaging (MRI) scan computes the stereotactic frame that would be used to accurately inoculate virus into a tumor at one or more locations. Virus would be inoculated at a dose of $10^1$ to $10^7$ p.f.u. per inoculation using a <2 mm cannula. The number of sites inoculated would depend on the size of the tumor. Patients would be followed with periodic MRI scans and with neurological examination, blood count, and liver function tests.

In an alternative strategy, patients will be operated to remove much of the recurrent tumor and virus will inoculated in the resected tumor bed in a fashion similar to above.

EXAMPLE 6

REPLICATION-COMPETENT HERPES SIMPLEX VIRUS VECTOR VACCINES

The herpes simplex virus vector of the invention can be used as a vaccine to protect an animal against herpes simplex virus infection. In the present context, "protecting" a subject against herpes simplex virus includes both (1) a prophylactic vaccine, i.e., a vaccine used to prevent a future herpes simplex virus infection, and (2) a therapeutic vaccine for treating an existing herpes simplex viral infection.

The herpes simplex virus sample would be prepared using standard methodology. Herpes simplex virus-infected Vero cells would be frozen at −70° C. until they are to be used. The material would be thawed and the cell debris would be pelleted by centrifugation. The supernatant fluid would be discarded and the pellet resuspended to its original volume. This material would most closely approximate that used in vaccine manufacture. This suspension would be sonicated twice for 20 seconds.

Herpes simplex virus plaque titers would be determined by standard procedures. For example, the virus would be titrated in triplicate on monolayers of Vero cells in 6-well plates. After adsorption of samples for 2 hours, cells would be overlayed with media containing 0.6% agarose and incubated at 37° C. in a $CO_2$-rich environment for 48 h. A second overlay, the same as above except for addition of neutral red, would be added and the cells would be incubated an additional 24 hours.

The herpes simplex virus pools would be titrated before filtration. The pools then would be filtered through a Nalgene 0.45 μm filter, sampled, refiltered through a second filter and then resampled.

EXAMPLE 7

TESTING OF HERPES SIMPLEX VIRUS-VACCINE FOR PATHOGENICITY IN A MURINE MODEL AND MONKEY MODEL

The lethality of the herpes simplex virus vaccine would be compared with the lethality of other herpes simplex virus vaccines in <24 h old suckling mice, CD-1 strain, (Charles River, Raliegh, N.C.). Meignier et al., J. Infect. Diseases 158: 602 (1988); Burke, Curr. Topics in Microbiology and Immunology 179: 137 (1992). Comparative titration of herpes simplex virus vector vaccine and wild type vaccines would be conducted in a single test using the final bulk of the herpes simplex virus vaccine.

Logarithmic dilutions of the vaccine would be prepared. Two litters of 5 mice each would be used for each dilution. Mice would be inoculated intracerebrally with 0.03 ml of the appropriate dilutions and observed for 21 days. Mouse lethality would be calculated as the dose in pfu that killed 50% of mice (e.g., pfu/0.03 ml of vaccine divided by $LD_{50}$ of vaccine).

Also, the herpes simplex virus vector would be given to 4 monkeys in the study. An additional six monkeys would receive the vector one year after immunization with the herpes simplex virus vector of the invention. If intradermal and subcutaneous administration of the vaccine candidate is well tolerated, the herpes simplex virus vector vaccine is deemed to be safe for use as an immunoprotective agent against herpes simplex virus.

In addition, all monkeys would be tested for serum antibody titers specific for herpes simplex virus. Monkey seroconversion would be measured by ELISA, after primary immunization. If all monkeys seroconvert, the herpes simplex virus vector vaccine is deemed to have efficacy as an immunoprotective agent against herpes simplex virus.

EXAMPLE 8

HUMAN CLINICAL STUDIES WITH HERPES SIMPLEX VIRUS VECTOR VACCINE

For use as a vaccine, the mutated herpes simplex virus vector of the invention would be inoculated subcutaneously. Thereafter, herpes simplex virus-specific antibody titers and herpes simplex virus-specific cell mediated response levels would be determined. Meignier et al., J. Infect. Diseases 162: 313 (1990); Burke, Curr. Topics in Microbiology and Immunology 179: 137 (1992). The preliminary phase of the study would involve an inoculation of four individuals with documented HSV-1 infections (Group 1), succeeded by inoculation of four HSV-1-naive individuals (Group 2) 21 days after the first group had been inoculated. Previous HSV-1 exposure would be documented by medical records or unequivocal HSV-1 outbreak, as assessed by HSV-1 immunofluorescence assay available in clinical laboratories. This would be followed by a randomized trial in 24 herpes simplex virus-naive volunteers (Group 3). Anti HSV-1 immune globulin and anti-herpetic agents are available on site for the treatment of serious adverse reactions.

Group 1, 2, 3 and 4 subjects would be admitted to the hospital three days prior to inoculation and would remain as inpatients until four days after inoculation. Subjects would then be discharged and assessed on an outpatient basis with clinical examinations for potential reactions or complications through day 21. Subjects developing fever, rash, lethargy, necrotic skin lesions, or neurologic signs are followed with subsequent daily clinical examinations and admitted to the hospital if deemed necessary.

Group 5 volunteers, all HSV-1-naive, would be enrolled depending on availability as outpatient subjects. Group 5 volunteers would be randomly assigned to one of two subgroups: one would receive a single injection and the other would receive a booster.

Protocol participation studies would include periodic examinations of the following: CBC with differential and platelets, urinalysis, serum chemistries, serum viremia, serum herpes simplex virus antibody, and lymphocyte immune responses to herpes simplex virus antigen. Remaining serum samples would be maintained frozen at −80° to −120° C. and available for additional studies and/or repeats of selected studies as needed. Fluid in vesicular or weeping lesions at the site of inoculation or at distant sites would be sampled and placed in viral isolation transport medium to attempt virus recovery. Serum antibody determinations would include ELISA reactivity with cells infected with the herpes simplex virus vector, HSV-1 antigen and plaque reduction neutralization of HSV-1 viral vector.

Clinical trials of the herpes simplex virus vector should show the vaccine to be safe and effective in humans. Vaccine recipients would be expected to produce significant humoral response as measured by ELISA. A positive response would be characterized by the production of both neutralizing and non-neutralizing antibodies, the latter being measured by plaque reduction and neutralization assays. In addition, positive lymphocyte blastogenesis assays would be expected to demonstrate that lymphocytes from vaccine recipients proliferate and produce cytokines upon exposure to herpes simplex virus antigen in vitro.

It is to be understood that the description, specific examples and data, while indicating preferred embodiments, are given by way of illustration and exemplification and are not intended to limit the present invention. Various changes and modifications within the present invention will become apparent to the skilled artisan from the discussion and diclosure contained herein.

What is claimed is:

1. A replication-competent herpes simplex virus comprising a tumor-specific or tissue-specific or cell-specific transcriptional regulatory sequence that is operatively linked to an essential herpes simplex virus gene, transcriptional regulatory sequence that is operatively linked to an essential herpes simplex virus gene, wherein said transcriptional regulatory sequence effects expression of said gene in a specific tumor, tissue or cell, such that said virus replicates only in said tumor, tissue or cell.

2. A herpes simplex virus vector, wherein the genome of said viral vector contains a tumor-specific or tissue-specific or cell-specific transcriptional regulatory sequence that is operatively linked to an essential herpes simplex virus gene, wherein said transcriptional regulatory sequence effects expression of said gene in a specific tumor, tissue or cell, such that said virus replicates only in said tumor, tissue or cell.

3. A method for killing tumor cells in a subject, comprising the step of administering to said tumor cells a pharmaceutical composition that is comprised of (A) a herpes simplex virus that contains a tumor-specific promoter that is operatively linked to an essential herpes simplex virus gene; and (B) a pharmaceutically acceptable vehicle for said virus, such that said tumor cells are infected in situ by said virus, whereby said tumor cells are killed.

4. The method of claim 3, wherein said tumor cells are of a type selected from the group consisting of melanoma cells, pancreatic cancer cells, prostate carcinoma cells, breast cancer cells, lung cancer cells, colon cancer cells, lymphoma cells, hepatoma cells, mesothelioma and epidermoid carcinoma cells.

5. A method fo preparing a tumor-specific or tissue-specific or cell-specific replication-competent herpes simplex virus, said method comprising the step of:

permanently altering the genome of a herpes simplex virus so that the virus (1) kills tumor cells and (2) lacks general virulence against normal cells and (3) contains a tumor-specific or tissue-specific or cell-specific transcriptional regulatory sequence that is operatively linked to an essential herpes simplex virus gene.

6. The method of claim 5, wherein said herpes simplex virus is HSV-1.

7. The method of claim 5, wherein said herpes simplex virus is HSV-2.

8. A method for ablating specific normal cells in a subject, comprising the step of administering to said cells a pharmaceutical composition composed of (A) a herpes simplex virus that contains a tissue-specific or cell-specific transcriptional regulatory sequence that is operatively linked to an essential herpes simplex virus gene, wherein said transcriptional regulatory sequence effects expression of said gene in a specific tissue or cell, such that said virus replicates only in said tissue or cell; and (B) a pharmaceutically acceptable vehicle for said virus, such that said specific normal cells are infected in situ by said virus, whereby said cells are killed.

9. The method of claim 8, wherein said normal cells are pituitary cells and said cell-specific transcriptional regulatory sequence is the growth hormone promoter.

10. The method of claim 8, wherein said normal cells are adrenocortical cells and said cell-specific transcriptional regulatory sequence is the Pro-opiomelanocortin promoter.

11. A method for killing tumor cells in a subject, comprising the steps of administering to said tumor cells a herpes simplex virus, wherein said virus comprises a tumor cell-specific transcriptional regulatory sequence wherein said transcriptional regulatory sequence controls expression of at least one viral protein necessary for viral replication and wherein said transcriptional regulatory sequence in said virus is induced selectively so that said virus replicates in the tumor cells at a level that is at least about two log orders higher than in normal cells, whereby said tumor cells are killed.

12. The replication-competent herpes simplex virus of claim 1, wherein said essential herpes simplex virus gene is an HSV immediate-early gene.

13. The replication-competent herpes simplex virus of claim 12, wherein said HSV immediate-early gene is the ICP4 gene.

* * * * *